US009277865B2

(12) United States Patent
Yamaguchi et al.

(10) Patent No.: US 9,277,865 B2
(45) Date of Patent: Mar. 8, 2016

(54) ESTIMATING APPARATUS AND ESTIMATING METHOD

(75) Inventors: Takashi Yamaguchi, Kanagawa (JP); Shiho Hakomori, Kanagawa (JP); Koshi Tamamura, Tokyo (JP); Tsunenori Arai, Kanagawa (JP); Arisa Ito, Kanagawa (JP); Jun Uchiyama, Kanagawa (JP)

(73) Assignee: ARAI MEDPHOTON RESEARCH LABORATORIES, CORPORATION, Kanagawa (JP)

( * ) Notice: Subject to any disclaimer, the term of this patent is extended or adjusted under 35 U.S.C. 154(b) by 306 days.

(21) Appl. No.: 13/583,531

(22) PCT Filed: Mar. 7, 2011

(86) PCT No.: PCT/JP2011/001330
§ 371 (c)(1),
(2), (4) Date: Oct. 23, 2012

(87) PCT Pub. No.: WO2011/114653
PCT Pub. Date: Sep. 22, 2011

(65) Prior Publication Data
US 2013/0123642 A1 May 16, 2013

(30) Foreign Application Priority Data

Mar. 15, 2010 (JP) .................................. 2010-058385
Dec. 10, 2010 (JP) .................................. 2010-275511

(51) Int. Cl.
*A61B 6/00* (2006.01)
*A61B 5/00* (2006.01)
(Continued)

(52) U.S. Cl.
CPC .............. *A61B 5/0071* (2013.01); *A61B 5/0084* (2013.01); *A61B 5/4848* (2013.01);
(Continued)

(58) Field of Classification Search
CPC .................... A61N 5/062; A61B 2017/22087; A61B 18/24; A61B 5/14556
USPC ........................................ 600/312; 604/890.1
See application file for complete search history.

(56) References Cited

U.S. PATENT DOCUMENTS 5,350,375 A 9/1994 Deckelbaum et al.
5,851,225 A * 12/1998 Lawandy ........................ 607/88
(Continued)

FOREIGN PATENT DOCUMENTS

JP 10-216252 8/1998
JP 2001-004542 1/2001
(Continued)

OTHER PUBLICATIONS

European Patent Office, Extended European Search Report issued in connection with European Patent Application No. 11755846.0, dated Jul. 25, 2013. (9 pages).

*Primary Examiner* — Anhtuan T Nguyen
*Assistant Examiner* — Jae Woo
(74) *Attorney, Agent, or Firm* — K&L Gates LLP

(57) ABSTRACT

A photodynamic therapy apparatus as an estimating apparatus is an apparatus for irradiating a tissue having absorbed photo-sensitive pharmaceutical, the photo-sensitive pharmaceutical absorbing an excitation light and emitting fluorescence, with the excitation light emitted from a tip portion of a laser catheter, including a connector, a light source, and a light detection unit. The laser catheter is capable of being attached to and detached from the connector. The light source outputs the excitation light to the laser catheter via the connector. The light detection unit detects intensity or a spectrum of the fluorescence, the fluorescence being entered from the laser catheter via the connector, to estimate whether the tissue has changed because of reaction between the excitation light emitted from the tip portion of the laser catheter and the photo-sensitive pharmaceutical absorbed in the tissue.

16 Claims, 30 Drawing Sheets

(51) Int. Cl.
*A61N 5/06* (2006.01)
*A61B 18/24* (2006.01)
*A61B 18/00* (2006.01)
*A61B 5/0402* (2006.01)

(52) U.S. Cl.
CPC ............. *A61B5/6852* (2013.01); *A61B 5/6869* (2013.01); *A61N 5/0601* (2013.01); *A61N 5/062* (2013.01); *A61B 5/0402* (2013.01); *A61B 18/24* (2013.01); *A61B 2018/00351* (2013.01); *A61N 2005/0602* (2013.01); *A61N 2005/0626* (2013.01)

(56) References Cited

U.S. PATENT DOCUMENTS

| | | | | |
|---|---|---|---|---|
| 6,030,411 | A * | 2/2000 | Lawandy | 607/88 |
| 6,123,719 | A * | 9/2000 | Masychev | 600/407 |
| 6,514,277 | B1 * | 2/2003 | Lilge et al. | 607/88 |
| 6,542,524 | B2 * | 4/2003 | Miyake | 372/23 |
| 6,749,623 | B1 * | 6/2004 | Hsi et al. | 607/88 |
| 6,899,723 | B2 * | 5/2005 | Chen | 607/88 |
| 8,088,534 | B2 | 1/2012 | Kimoto | |
| 2006/0282132 | A1 * | 12/2006 | Arai et al. | 607/88 |
| 2009/0042238 | A1 * | 2/2009 | Sakurai et al. | 435/29 |
| 2009/0054883 | A1 * | 2/2009 | Stolen et al. | 606/14 |
| 2010/0022998 | A1 * | 1/2010 | Arai et al. | 606/15 |
| 2011/0238002 | A1 * | 9/2011 | Kurkayev | 604/21 |
| 2012/0209125 | A1 * | 8/2012 | Davis et al. | 600/476 |

FOREIGN PATENT DOCUMENTS

| | | |
|---|---|---|
| JP | 2006-167046 | 6/2006 |
| WO | 97/15226 | 5/1997 |
| WO | 2004/112902 | 12/2004 |
| WO | 2007/116582 | 10/2007 |
| WO | 2008/066126 | 6/2008 |
| WO | 2009/025826 | 2/2009 |
| WO | 03/061696 | 7/2013 |

* cited by examiner

FIG.18
(a)
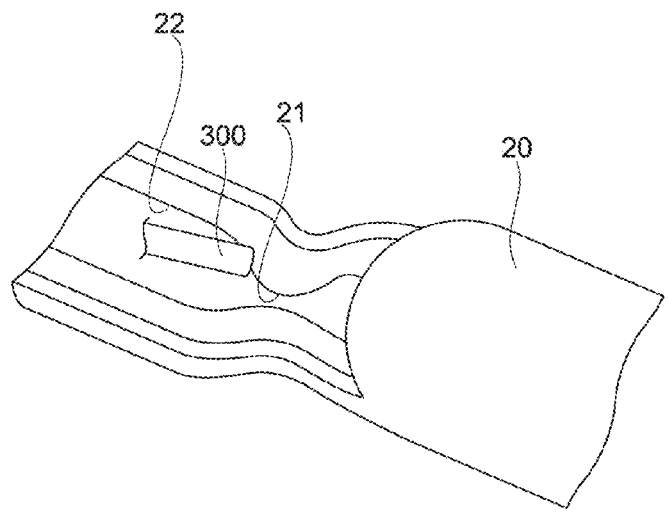
(b)
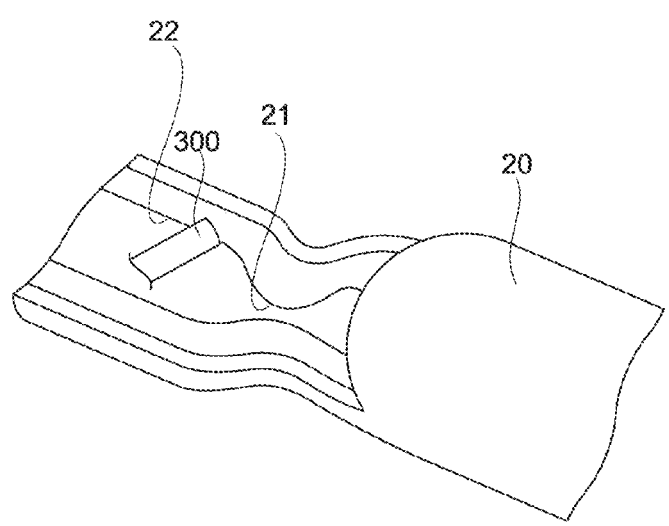
FIG.19
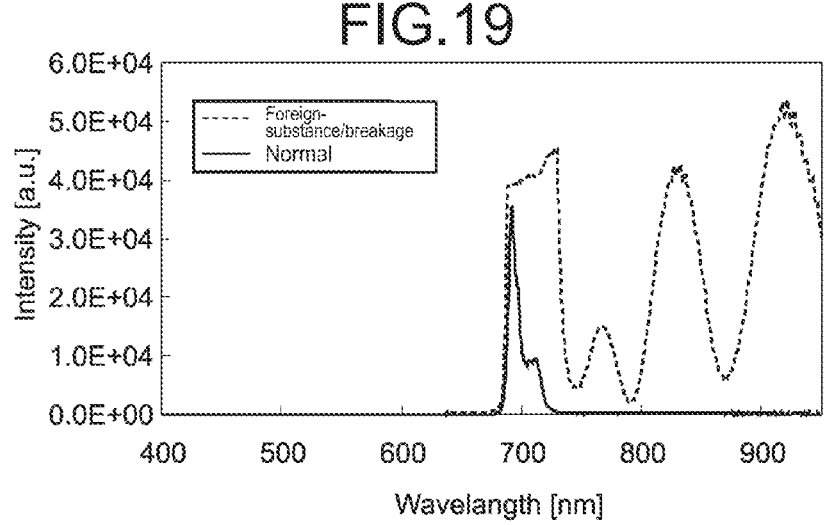

FIG.25

$$\boxed{\int_0^T [{}^1O_2](t)\,dt} = \int_0^T \left( [S_0]_t(t) \times v\rho\,\sigma t \times \frac{k_{ics}}{k_f + k_{ics}} \times \frac{k_q[{}^3O_2]}{\frac{1}{\tau_0} + k_q[{}^3O_2]} \right) dt$$

$$\frac{d[S_0]_t(t)}{dt} = -k_b [S_0]_t(t)[{}^1O_2](t)$$

$$\rho = I \times G(d, t, t')$$

$$[S_0]_t(t) = F(PS\ dose, t, t')$$

t : Irradiation time period in each site
t' : Elapsed time after pharmaceutical administration (iv)
ρ : Light density at depth d

FIG.33

$$\frac{P_{fl}^{b} - P(t)}{P_{fl}^{b} - P_{fl}^{t}} \times 100 = \text{Contact level}$$

ESTIMATING APPARATUS AND ESTIMATING METHOD

CROSS REFERENCES TO RELATED APPLICATIONS

The present application is a national stage of International Application No. PCT/JP2011/001330 filed on Mar. 7, 2011 and claims priority to Japanese Patent Application No. 2010-058385 filed on Mar. 15, 2010, and Japanese Patent Application No. 2010-275511 filed on Dec. 10, 2010, the disclosure of which is incorporated herein by reference.

BACKGROUND

The present invention relates to an estimating apparatus and an estimating method that estimate process of therapy using a laser catheter.

Atrial fibrillation is known as a kind of tachyarrhythmia. A hyperexcited site, which generates an electrical pulse, appears in the vicinity of a root portion, in which a pulmonary vein and a left atrium are connected, and the left atrium minutely vibrates and contracts because of the electrical pulse stimulation, to thereby cause an atrial fibrillation.

As an atrial fibrillation therapeutic method, the inventors have been proposed application of photodynamic therapy (hereinafter, referred to as "PDT".) (for example, see Patent Document 1.). In PDT, a cardiac-muscle tissue, which has absorbed photo-sensitive pharmaceutical, is irradiated with an excitation light by using a laser catheter, to thereby generate singlet oxygen. The singlet oxygen as a strong oxidizer insults a cardiac-muscle tissue, which surrounds the hyperexcited site, to thereby form an electric-conduction block, which blocks conduction of the electrical pulse from the hyperexcited site to the left atrium. As a result, an electric conduction between the hyperexcited site and the left atrium is blocked, and an abnormal vibration and contraction of the left atrium is inhibited.

Photo-sensitive pharmaceutical has a property of selectively accumulating in a certain tissue. In view of this, in general, after a predetermined time (for example, 8 to 48 hours) passes after photo-sensitive pharmaceutical is administered in a patient, when the state where the photo-sensitive pharmaceutical concentration is high in a therapy-target tissue and the photo-sensitive pharmaceutical concentration is low in other tissues and blood is established, that is, when the state where a so-called photo-sensitive pharmaceutical contrast is high is established, irradiation with the excitation light is started. Further, recently, PDT, in which the accumulating property of photo-sensitive pharmaceutical is not used and in which irradiation with the excitation light is started when photo-sensitive pharmaceutical is delivered to a therapy-target tissue by blood, is proposed.

Patent Document 1: WIPO Publication No. 2008/066126

SUMMARY

Problem to be Solved by the Invention

As a method of estimating whether a tissue of an excitation-light-irradiated site is broken, whether an electric-conduction block is formed, and the like, there is known a method of leading a device such as a catheter having a detection means such as an electrode to an excitation-light-irradiated site, and performing estimation by using the catheter. However, because an irradiated site does not coincide with a potential-measured site precisely in therapy using a light, it is desired to provide means for estimating therapeutic effects more accurately in real time.

In view of the above-mentioned circumstances, an object of the present invention is to provide an estimating apparatus and an estimating method capable of estimating process of therapy using a laser catheter accurately in real time.

Means for Solving the Problem

To attain the above-mentioned object, an estimating apparatus according to an embodiment of the present invention is an apparatus for irradiating a tissue having absorbed photo-sensitive pharmaceutical, the photo-sensitive pharmaceutical absorbing an excitation light and emitting fluorescence, with the excitation light emitted from a tip portion of a laser catheter, including a connector, a light source, and a detection unit.

The laser catheter is capable of being attached/detached to/from the connector.

The light source outputs the excitation light to the laser catheter via the connector.

The detection unit detects intensity of the fluorescence, the fluorescence being entered from the laser catheter via the connector, to estimate whether the tissue has changed because of reaction between the excitation light emitted from the tip portion of the laser catheter and the photo-sensitive pharmaceutical absorbed in the tissue.

By detecting the intensity of the fluorescence entered from the laser catheter, it is possible to estimate whether the tissue has changed because of the reaction between the excitation light and the photo-sensitive pharmaceutical in real time. As a result, it is possible to estimate process of therapy using a laser catheter. Further, by using a laser catheter used for therapy, operability is improved. Note that the phrase "tissue is changed" means, for example, insult to a tissue such as a cytocidal effect and an electric-conduction block, damage, thermal denaturation, and the like.

The detection unit may detect intensity of the fluorescence, the fluorescence being entered from the laser catheter via the connector, to simultaneously estimate whether the tissue has changed because of reaction between an excitation light emitted from the tip portion of the laser catheter and the photo-sensitive pharmaceutical absorbed in the tissue, and whether a contact state of the tip portion of the laser catheter with respect to the tissue has changed.

Specifically in intracardiac therapy using a laser catheter, the laser catheter moves affected by breathing or heartbeat, and the contact state with respect to a therapy-target tissue may change. According to this embodiment, the change of a cardiac-muscle tissue and the contact state of the tip portion of the laser catheter are monitored in real time, and an irradiation condition may be set/changed according to the situation.

The estimating apparatus may further include a controller for simultaneously estimating whether the tissue has changed because of reaction between an excitation light emitted from the tip portion of the laser catheter and the photo-sensitive pharmaceutical absorbed in the tissue, and a contact state of the tip portion of the laser catheter with respect to the tissue, based on the detected intensity of the fluorescence.

By detecting the intensity of fluorescence entered from the laser catheter, the change of the tissue because of reaction between the excitation light and the photo-sensitive pharmaceutical, and the contact state of the tip portion of the laser catheter with respect to a tissue may be estimated in real time.

The controller may visually reflect a current-estimated-result of the change of the tissue in a peak-estimated-result of the change of the tissue, and output a signal for simultaneously informing of the estimated result of the change of the tissue and the estimated result of the contact state.

Here, to "output a signal" means, for example, to output a display instruction including display information to a display unit. As a result, a practitioner may recognize the current-estimated-result of the change of the tissue and the contact state of the tip portion of the laser catheter simultaneously and intuitively. As a result, during therapeutic-light irradiation, a practitioner may recognize, in real time, that the tip portion of the laser catheter is displaced affected by heartbeat or breathing, and may control the posture promptly. Simultaneously, a practitioner may understand the estimated result of the change of the tissue, which may vary according to individual variability and therapy-target sites, accurately in real time, and perform the operation. A practitioner needs to determine everything with reference to a plurality of screens during an operation. So it is helpful for a trouble-free operation by a practitioner to display the current-estimated-result of the change of the tissue and the contact state of the tip portion of the laser catheter in an intuitively-recognizable mode.

The estimating apparatus may further include storage for storing the peak-estimated-result of the change of the tissue.

The controller may record the current-estimated-result of the change of the tissue in the storage, updates, in a case where the current-estimated-result of the change of the tissue is equal to or larger than the peak-estimated-result of the change of the tissue recorded in the storage, the peak-estimated-result of the change of the tissue recorded in the storage with the current-estimated-result of the change of the tissue, and output a signal for simultaneously informing of the estimated result of the change of the tissue and the estimated result of the contact state, by displaying the current-estimated-result of the change of the tissue on the updated peak-estimated-result of the change of the tissue in an overlapped manner.

By displaying the current-estimated-result of the change of the tissue on the peak-estimated-result of the change of the tissue in an overlapped manner, a practitioner may recognize the difference between the peak-estimated-result and the current-estimated-result intuitively as the change of the contact state of the tip portion of the laser catheter. For example, a practitioner may intuitively recognize that the contact state of the tip portion of the laser catheter has changed from the identical contact state, and that the tip portion of the laser catheter is removed from a tissue and drifts in blood.

The estimating apparatus may further include a controller for estimating whether the tissue has changed because of reaction between the excitation light emitted from the tip portion of the laser catheter and the photo-sensitive pharmaceutical absorbed in the tissue, based on intensity of the detected fluorescence.

By detecting the intensity of the fluorescence entered from the laser catheter, it is possible to estimate whether the tissue has changed because of the reaction between the excitation light and the photo-sensitive pharmaceutical in real time.

The controller may output a signal for informing whether the tissue has changed, based on the estimated result.

As a result, it is possible to inform a practitioner whether a tissue has changed in real time, based on the intensity of the fluorescence entered from the laser catheter. Note that to "output a signal" means to output a display instruction including display information to a display unit, or to output a sound output instruction to a speaker unit.

The controller may output a signal to prompt to change an irradiation condition of the excitation light, based on the estimated result.

As a result, it is possible to prompt a practitioner to change an irradiation condition of the excitation light in real time, based on the intensity of the fluorescence entered from the laser catheter.

The controller may obtain an electrocardiographic signal, and estimates whether the tissue has changed, based on a correlation between the electrocardiographic signal and the intensity of the fluorescence.

By calculating the correlation between the electrocardiographic signal and the intensity of the fluorescence, it is possible to determine whether a tissue has changed in real time.

An estimating apparatus for therapy for atrial fibrillation according to an embodiment of the present invention is an apparatus for irradiating a cardiac-muscle tissue having absorbed photo-sensitive pharmaceutical, the photo-sensitive pharmaceutical absorbing an excitation light and emitting fluorescence, with the excitation light emitted from a tip portion of a laser catheter, including a connector, a light source, and a detection unit.

The laser catheter is capable of being attached/detached to/from the connector.

The light source outputs the excitation light to the laser catheter via the connector.

The detection unit detects intensity of the fluorescence, the fluorescence being entered from the laser catheter via the connector, to estimate whether the cardiac-muscle tissue is changed because of reaction between the excitation light emitted from the tip portion of the laser catheter and the photo-sensitive pharmaceutical absorbed in the cardiac-muscle tissue.

By detecting the intensity of the fluorescence entered from the laser catheter, it is possible to estimate whether the tissue has changed because of the reaction between the excitation light and the photo-sensitive pharmaceutical in real time. As a result, it is possible to estimate process of therapy for atrial fibrillation using a laser catheter. Further, by using a laser catheter used for therapy, operability is improved.

The detection unit may detect intensity of the fluorescence, the fluorescence being entered from the laser catheter via the connector, to simultaneously estimate whether the cardiac-muscle tissue has changed because of reaction between an excitation light emitted from the tip portion of the laser catheter and the photo-sensitive pharmaceutical absorbed in the cardiac-muscle tissue, and whether a contact state of the tip portion of the laser catheter with respect to the cardiac-muscle tissue has changed.

The estimating apparatus may further include a controller for simultaneously estimating whether the cardiac-muscle tissue has changed because of reaction between an excitation light emitted from the tip portion of the laser catheter and the photo-sensitive pharmaceutical absorbed in the cardiac-muscle tissue, and a contact state of the tip portion of the laser catheter with respect to the cardiac-muscle tissue, based on the detected intensity of the fluorescence.

The controller may visually reflect a peak-estimated-result of the change of the cardiac-muscle tissue in a current-estimated-result of the change of the cardiac-muscle tissue, and outputs a signal for simultaneously informing of the estimated result of the change of the cardiac-muscle tissue and the estimated result of the contact state.

The estimating apparatus may further include storage for storing the peak-estimated-result of the change of the cardiac-muscle tissue.

The controller may record the current-estimated-result of the change of the cardiac-muscle tissue in the storage, update, in a case where the current-estimated-result of the change of the cardiac-muscle tissue is equal to or larger than the peak-estimated-result of the change of the cardiac-muscle tissue recorded in the storage, the peak-estimated-result of the change of the cardiac-muscle tissue recorded in the storage with the current-estimated-result of the change of the cardiac-muscle tissue, and output a signal for simultaneously informing of the estimated result of the change of the cardiac-muscle tissue and the estimated result of the contact state, by displaying the current-estimated-result of the change of the cardiac-muscle tissue on the updated peak-estimated-result of the change of the cardiac-muscle tissue in an overlapped manner.

An estimating method according to an embodiment of the present invention includes irradiating a tissue having absorbed photo-sensitive pharmaceutical, the photo-sensitive pharmaceutical absorbing an excitation light and emitting fluorescence, with the excitation light emitted from a tip portion of a laser catheter.

The fluorescence corresponding to the irradiated excitation light is extracted via the laser catheter.

Whether the tissue has changed because of reaction between the excitation light emitted from the tip portion of the laser catheter and the photo-sensitive pharmaceutical absorbed in the tissue is estimated, based on intensity of the extracted fluorescence.

By detecting the intensity of the fluorescence entered from the laser catheter, it is possible to estimate whether the tissue has changed because of the reaction between the excitation light and the photo-sensitive pharmaceutical in real time. As a result, it is possible to estimate process of therapy using a laser catheter.

The estimating method may further include simultaneously estimating whether the tissue has changed because of reaction between an excitation light emitted from the tip portion of the laser catheter and the photo-sensitive pharmaceutical absorbed in the tissue, and a contact state of the tip portion of the laser catheter with respect to the tissue, based on the extracted intensity of the fluorescence.

The estimating method may further include visually reflecting a current-estimated-result of the change of the tissue in a peak-estimated-result of the change of the tissue, and outputting a signal for simultaneously informing of the estimated result of the change of the tissue and the estimated result of the contact state.

The estimating method may further include recording the current-estimated-result of the change of the tissue in storage, updating, in a case where the current-estimated-result of the change of the tissue is equal to or larger than the peak-estimated-result of the change of the tissue recorded in the storage, the peak-estimated-result of the change of the tissue recorded in the storage with the current-estimated-result of the change of the tissue, and outputting a signal for simultaneously informing of the estimated result of the change of the tissue and the estimated result of the contact state, by displaying the current-estimated-result of the change of the tissue on the updated peak-estimated-result of the change of the tissue in an overlapped manner.

The estimating method may further include obtaining an electrocardiographic signal, and estimating whether the tissue has changed, based on a correlation between the electrocardiographic signal and the intensity of the fluorescence.

By calculating the correlation between the electrocardiographic signal and the intensity of the fluorescence, it is possible to determine whether the tissue has changed because of reaction between the excitation light and the photo-sensitive pharmaceutical in real time.

An estimating method according to an embodiment of the present invention is an estimating method using photo-sensitive pharmaceutical absorbing an excitation light and emitting a fluorescence, a laser catheter capable of emitting the excitation light from a tip portion, and an estimating apparatus including a connector to/from which the laser catheter is capable of being attached/detached and a light source for outputting the excitation light to the laser catheter via the connector.

In a tissue, the photo-sensitive pharmaceutical is absorbed.

The tip portion of the laser catheter is led to the tissue having absorbed the photo-sensitive pharmaceutical, the laser catheter being attached to the connector.

The tissue having absorbed the photo-sensitive pharmaceutical is irradiated with the excitation light emitted from the tip portion of the laser catheter, the excitation light being output from the light source.

The fluorescence corresponding to the irradiated excitation light is extracted via the laser catheter.

Whether the tissue has changed because of reaction between the excitation light emitted from the tip portion of the laser catheter and the photo-sensitive pharmaceutical absorbed in the tissue is estimated, based on intensity of the extracted fluorescence.

The estimating method may further include simultaneously estimating whether the tissue has changed because of reaction between an excitation light emitted from the tip portion of the laser catheter and the photo-sensitive pharmaceutical absorbed in the tissue, and a contact state of the tip portion of the laser catheter with respect to the tissue, based on the extracted intensity of the fluorescence.

The estimating method may further include visually reflecting a current-estimated-result of the change of the tissue in a peak-estimated-result of the change of the tissue, and outputting a signal for simultaneously informing of the estimated result of the change of the tissue and the estimated result of the contact state.

The estimating method may further include recording the current-estimated-result of the change of the tissue in storage, updating, in a case where the current-estimated-result of the change of the tissue is equal to or larger than the peak-estimated-result of the change of the tissue recorded in the storage, the peak-estimated-result of the change of the tissue recorded in the storage with the current-estimated-result of the change of the tissue, and outputting a signal for simultaneously informing of the estimated result of the change of the tissue and the estimated result of the contact state, by displaying the current-estimated-result of the change of the tissue on the updated peak-estimated-result of the change of the tissue in an overlapped manner.

The estimating method may further include obtaining an electrocardiographic signal, and estimating whether the tissue has changed, based on a correlation between the electrocardiographic signal and the intensity of the fluorescence.

Effect of the Invention

According to the present invention, it is possible to estimate process of therapy using a laser catheter accurately in real time, and to perform the therapy reliably.

Additional features and advantages are described herein, and will be apparent from the following Detailed Description and the figures.

BRIEF DESCRIPTION OF THE FIGURES

FIG. 18 Schematic diagrams each showing a contact state of a laser catheter in an intravascular lumen.

FIG. 19 A graph showing the relation between wavelength and fluorescence intensity.

FIG. 25 A diagram for explaining formulae for setting concentration and an irradiation power during pharmaceutical administration.

FIG. 33 A formula for calculating the contact level of the tip portion of the laser catheter with respect to an inner wall of a tissue.

DETAILED DESCRIPTION

Hereinafter, embodiments of the present invention will be described with reference to the drawings. In the embodiments, the case where a photodynamic therapy apparatus (hereinafter referred to as "PDT apparatus".) is used as an estimating apparatus will be described.

First Embodiment

Figure 1:
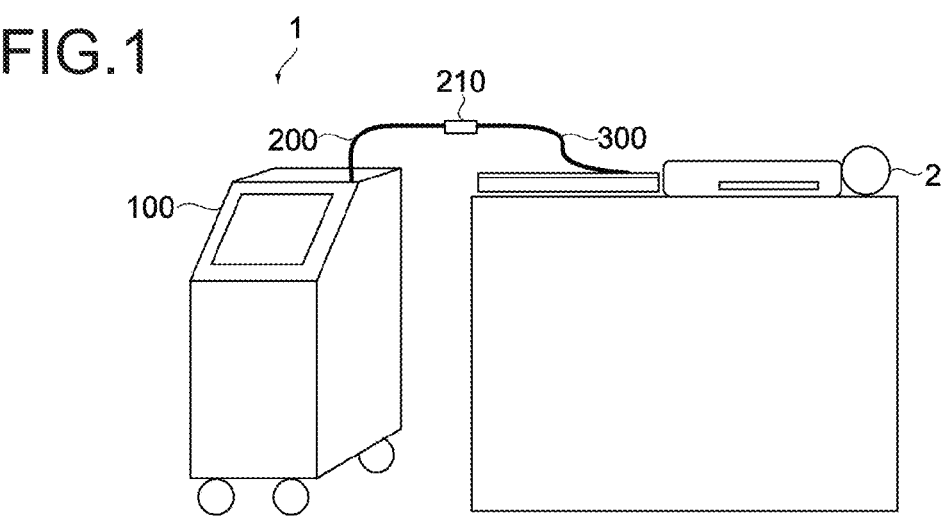
FIG. 1 A schematic diagram showing a PDT apparatus according to a first embodiment of the present invention.

FIG. 1 is a schematic diagram showing a PDT apparatus according to a first embodiment of the present invention.

The PDT apparatus 1 includes a PDT apparatus main body 100, a tube 200 connected to the PDT apparatus main body 100, and a connector 210 provided on the end of the tube 200.

Figure 3:
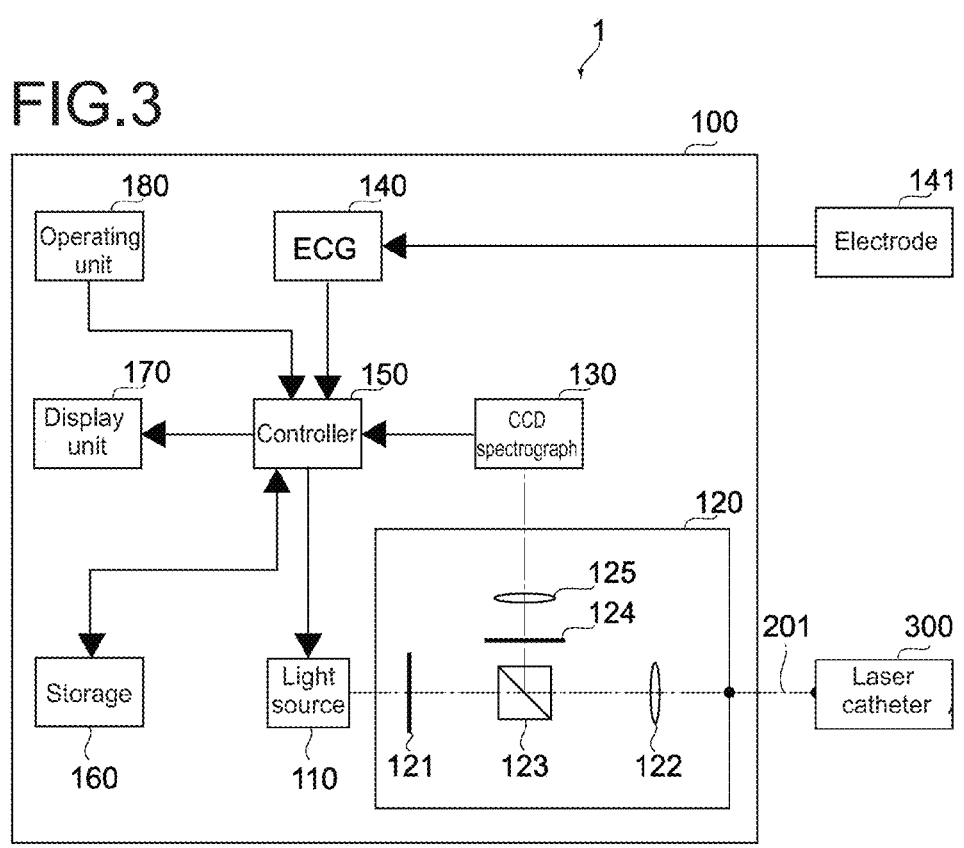
FIG. 3 A block diagram showing a PDT apparatus main body.

The tube 200 is a soft hollow tube, and is capable of transmitting light via an inner apparatus-attached optical fiber 201 (see FIG. 3.).

A laser catheter 300 is detachably connected to the connector 210.

Photo-sensitive pharmaceutical is administered to a patient 2. In the case of being administered by intravenous injection, the administered photo-sensitive pharmaceutical diffuses in the blood, and then a tissue such as a cardiac-muscle tissue absorbs the pharmaceutical. A dose of photo-sensitive pharmaceutical necessary for therapy may be administered at one time by intravenous injection, may be administered continuously by intravenous drip, may be administered at one time or continuously via the oral route, or may be administered locally. Photo-sensitive pharmaceutical is pharmaceutical that absorbs light having a certain wavelength, is photoexcited, and becomes fluorescent. For example, pharmaceutical called talaporfin sodium (Laserphyrin (registered trademark), Meiji Co., Ltd.) is employed. Because the Q-band absorption wavelength of this pharmaceutical is near 664 nm, an excitation light source for this pharmaceutical with, for example, 600 to 800 nm, preferably 660 to 680 nm, or more preferably 664 plus or minus 2 nm is used.

Figure 2:
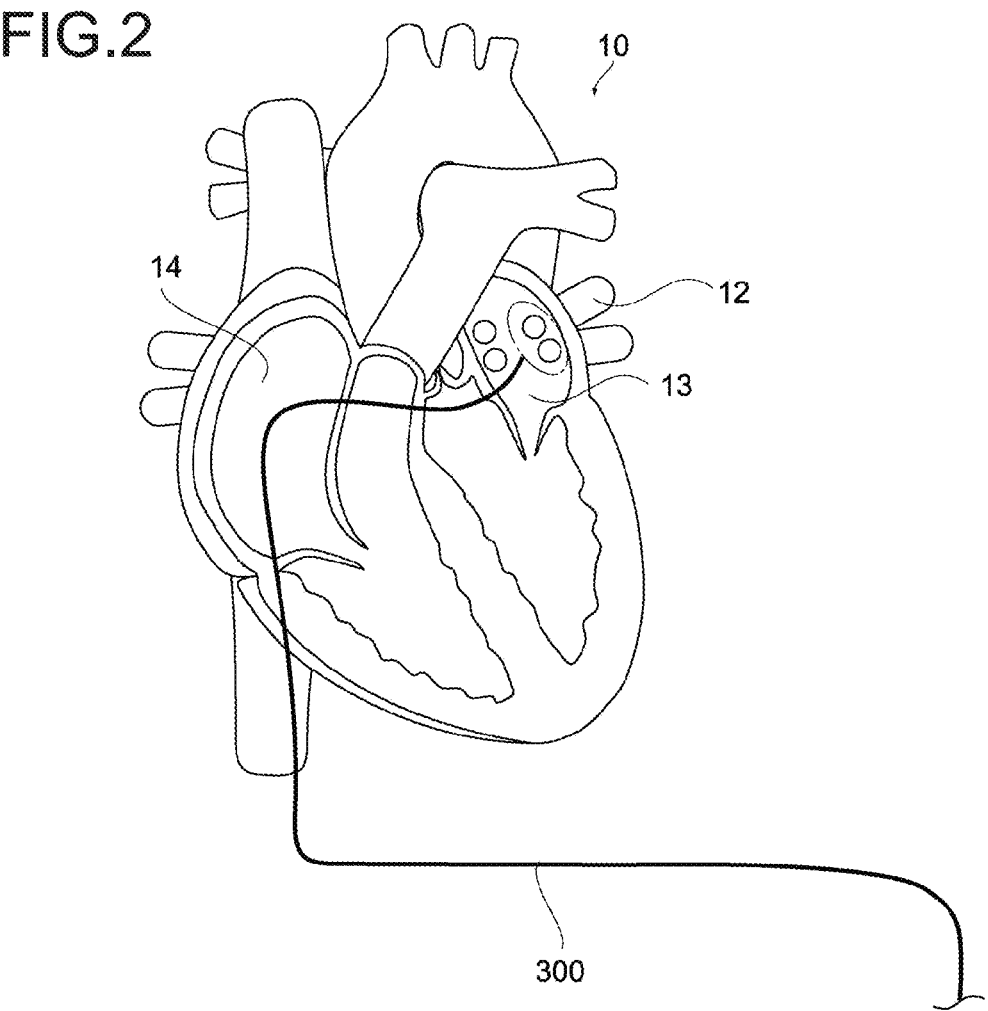
FIG. 2 A schematic diagram showing a laser catheter inserted in a heart.

FIG. 2 is a schematic diagram showing a laser catheter inserted in a heart.

The laser catheter 300 is inserted in a right atrium 14 of a heart 10 via a femoral vein or a jugular vein of the patient 2. The laser catheter 300, which has reached the right atrium 14, penetrates a septum, and is led to a left atrium 13.

[Configuration of PDT Apparatus Main Body]

FIG. 3 is a block diagram showing the PDT apparatus main body.

The PDT apparatus main body 100 includes a light source 110, an optical system 120, a detection unit 130, an electrocardiograph 140, a controller 150, storage 160, a display unit 170, and an operating unit 180.

The light source 110 outputs an excitation light for photo-sensitive pharmaceutical. The wavelength of the light output by the light source 110 is the same as the Q-band absorption wavelength of the photo-sensitive pharmaceutical. For example, in the case where photo-sensitive pharmaceutical whose Q-band absorption wavelength is near 664 nm is used, a semiconductor laser with the emission wavelength of 600 to 800 nm, preferably 660 to 680 nm, or more preferably 664 plus or minus 2 nm is used as the light source 110. The excitation light output by the light source 110 enters the laser catheter 300 via the optical system 120.

The optical system 120 allows the excitation light, which is emitted from the light source 110, to enter the laser catheter 300, which is connected to the connector 210 via the apparatus-attached optical fiber 201. The optical system 120 extracts, from the laser catheter 300, fluorescence emitted from photo-sensitive pharmaceutical, which is irradiated with the excitation light, and allows the fluorescence to enter the detection unit 130. The optical system 120 includes a short pass filter 121, a first lens 122, a polarizing beam splitter (hereinafter referred to as "PBS".) 123, a long pass filter 124, and a second lens 125.

The short pass filter 121 is a short-wavelength transmission filter with a cuton wavelength of 670 nm, and cuts long-wavelength radiation. The excitation light from the light source 110 has the radiation component in the fluorescence observation wavelength range (long-wavelength side of peak wavelength). In view of this, the radiation component of the excitation light in the long-wavelength side is cut at the stage prior to collecting the light in the laser catheter 300. The excitation light, which has passed the short pass filter 121, enters the first lens 122.

The first lens 122 collects the excitation light, which has entered from the short pass filter 121, on one edge of the laser catheter 300. Further, the first lens 122 collects fluorescence from the tip portion of the laser catheter 300 on the PBS 123. Note that part of the excitation light from the light source 110 is reflected off an edge of the apparatus-attached optical fiber 201 at the PDT apparatus main body 100 side, off the inside of the connector 210, and off the tip portion of the laser catheter 300, and enters the PBS 123 as specular reflection light. The specular reflection light is noisy when detecting fluorescence.

By using polarization differences, the PBS 123 allows the specular reflection light, which has reflected off an edge of the optical fiber in the tube 200, out of the light entered from the first lens 122, to pass through, does not detect the specular reflection light, reflects fluorescence and the specular reflection light reflected off the other edges, and brings them to a detecting device. The fluorescence, which has passed the PBS 123, enters the long pass filter 124.

The long pass filter 124 causes the specular reflection light, which has reflected off the inside of the connector 210 and the tip portion of the laser catheter 300, out of the light entered from the PBS 123, not to pass through, allows only the fluorescence to pass through, and brings the fluorescence to the detecting device. The fluorescence, which has passed through the long pass filter 124, enters the second lens 125.

The second lens 125 collects the fluorescence, which has entered from the long pass filter 124, on the detection unit 130.

The detection unit 130 is, for example, a linear image sensor, and spectroscopically detects the fluorescence entered from the optical system 120. That is, the detection unit 130 detects the light having the excitation wavelength, and detects the fluorescence from the photo-sensitive pharmaceutical, which is a light having a wavelength longer than the excitation wavelength. The detection unit 130 outputs an electrical signal, which shows intensity of the detected fluorescence, to the controller 150.

An electrode pad 141 is connected to the electrocardiograph 140 via an electrode code (not shown). The electrocardiograph 140 obtains an electrocardiographic signal of the patient 2 via the electrode pad 141, which is attached to the patient 2, and via the electrode code, and supplies the obtained electrocardiographic signal to the controller 150.

The controller 150 controls the respective units of the PDT apparatus 1.

The controller 150 calculates fluorescence intensity based on the electrical signal obtained from the detection unit 130. The controller 150 calculates pharmaceutical concentration in the tissue or in the blood based on the calculated fluorescence intensity (pharmaceutical-concentration-monitoring operation). The controller 150 determines whether to additionally administer the pharmaceutical or not based on the calculated pharmaceutical concentration.

The controller 150 determines the contact state of the laser catheter 300 with respect to the tissue based on the electrical signal obtained from the detection unit 130 (contact-monitoring operation).

The controller 150 determines, based on change of the fluorescence intensity during excitation light irradiation, whether an abnormal situation such as a foreign substance or a breakage occurs or not, and determines the cytocidal effect (foreign-substance/breakage-monitoring operation, and cytocidal-effect-determining operation). The controller 150 controls the light source 110 to stop irradiating the excitation light based on determination results.

The controller 150 determines whether an electric-conduction block is formed or not based on an electrical signal obtained from the detection unit 130 and based on an electrocardiographic signal obtained from the electrocardiograph 140 (electric-conduction-block-formation determining operation).

The controller 150 outputs, to the display unit 170, display instructions to display the above-mentioned various calculation results, the above-mentioned various determination results, and various information.

The storage 160 is a nonvolatile memory, and is set in, for example, a flash memory, an HDD (Hard Disk Drive), or another solid memory. The controller 150 records, in the storage 160, temporal change of fluorescence intensity, in which information on fluorescence intensity obtained from the detection unit 130 is in relation with time information obtained from a timing measurement unit (not shown), which measures the elapsed time after a criterion time such as excitation-light-irradiation start time. The controller 150 records, in the storage 160, electrocardiograms in which information on an electrocardiographic signal obtained from the electrocardiograph 140 is in relation with time information.

The display unit 170 is a display device, which uses, for example, a liquid-crystal display device or the like. When the display unit 170 obtains display instructions from the controller 150, the display unit 170 displays, on a display screen, for example, information on fluorescence intensity, information on an electrocardiographic signal, time information, and the like, based on display information in the display instructions.

The operating unit 180 receives instructions, which are input through operations by a practitioner, and outputs the received instructions to the controller 150. The instructions include, for example, instructions to turn on/off the excitation light output from the light source 110, to change intensity, and the like. As intensity of the excitation light, it is possible to select at least one of two levels of intensity including a first intensity, which has a low power (for example, optical output of 1 mW or less) and is minimally-invasive with respect to a tissue and blood, and a second intensity, which has a high power and is approximately 1,000 times higher than the first intensity. The first intensity is selected when monitoring the pharmaceutical concentration and the contact state of the laser catheter 300 before therapy. The second intensity is selected when therapy is conducted. Note that the first intensity is a fixed value, and the second intensity may be variable.

[Structure of Laser Catheter]

The laser catheter 300 outputs an excitation light from the tip portion.

Figure 4:
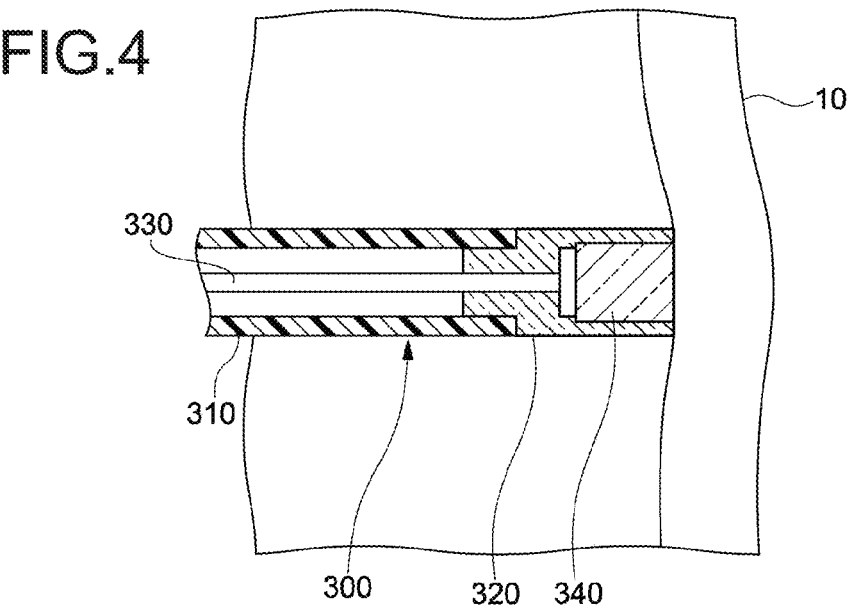
FIG. 4 A sectional view showing the tip portion of the laser catheter.

FIG. 4 is a sectional view showing the tip portion of the laser catheter.

The laser catheter 300 includes a catheter tube 310, a holder 320, an optical fiber 330, and an optical window 340.

The catheter tube 310 is a soft hollow tube, and is led to the inner wall of a cardiac-muscle tissue of the heart 10 of the patient 2. The catheter tube 310 has the optical fiber 330 therein.

The holder 320 is fixed to the catheter tube 310. The holder 320 holds the optical fiber 330 and the optical window 340 with respect to the catheter tube 310.

The optical fiber 330 is, for example, one quartz step index fiber having a core diameter of 133 μm and an outside diameter of 500 μm. The optical fiber 330 transmits the excitation light from the PDT apparatus 1. The optical fiber 330 outputs the transmitted excitation light, as an irradiation light 301, from the tip to the optical window 340. The beam diameter of the irradiation light 301 increases at the angle determined by the numerical aperture (NA) of the optical fiber 330. The tip of the optical fiber 330 is worked such that the beam diameter of the irradiation light 301 appropriately increases. The optical fiber 330 transmits the fluorescence, which is emitted from photo-sensitive pharmaceutical absorbed in a tissue and irradiated with an excitation light, to the PDT apparatus 1.

The optical window 340 is provided on the outermost of the tip portion of the laser catheter 300 such that the optical window 340 is optically connected to the tip of the optical fiber 330. The optical window 340 is made from a solid transparent material, for example, a glass material such as BK7. The optical window 340 as an irradiation section allows the irradiation light 301, which is output from the tip of the optical fiber 330, to pass through. The optical window 340 as a light-receiving section collects the fluorescence, which is emitted from the photo-sensitive pharmaceutical, on the tip of the optical fiber 330.

In order to detect fluorescence with a high SN (Signal-Noise) ratio, there is known a method of separately providing an irradiation fiber and a detection fiber in a laser catheter, and performing irradiation and light-reception, to thereby remove specular reflection light (see Japanese Patent Application Laid-open No. 2009-148550, paragraph [0037].).

Meanwhile, in the case of performing intracardiac therapy or diagnosis, in order to increase the curvature of a laser catheter, it is desirable that the diameter of a laser catheter be small. In the case of providing a plurality of optical fibers in a laser catheter, each optical fiber should be formed extra-finely, and thus a light having a necessary intensity may not be transmitted.

In view of the above, in diseases requiring intracardiac approaches such as, specifically, atrial fibrillation and ventricular flutter, it is desired that one optical fiber be in a laser catheter. Further, because it is necessary to detect fluorescence at intensity with a low power so as not to affect a living body, it is necessary to form a measurement system with a high SN (Signal-Noise) ratio by using one optical fiber.

In view of the above, according to the PDT apparatus 1 of this embodiment, the PBS 123 and the long pass filter 124 removes a specular reflection light on the fiber entrance edge, and the short pass filter 121 further removes a long-wavelength-side radiation component of a excitation light. With this structure, in the laser catheter 300, while the one optical fiber 330 doubles an irradiation fiber and a detection fiber, the detection unit 130 can detect fluorescence with a high SN ratio. As a result, it is possible to detect fluorescence with a low power so as not to affect a living body. Therefore, in the therapy and diagnosis of circulatory diseases, it is possible to perform minimally-invasive diagnoses with an extra-fine laser catheter with an increased curvature.

[Operations of PDT Apparatus]

Next, operations of the PDT apparatus 1 configured as described above will be described.

Figure 5:
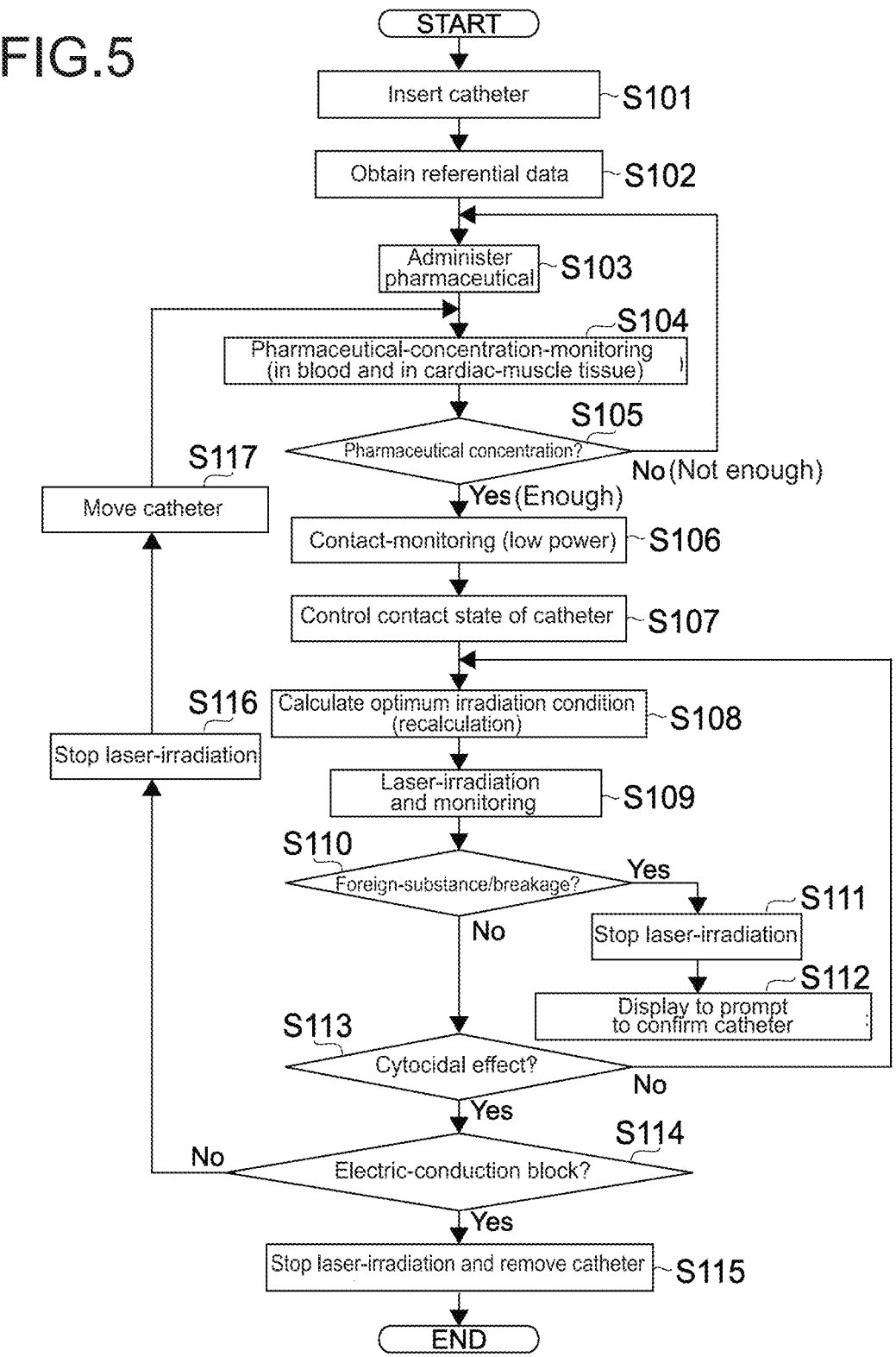
FIG. 5 A flowchart showing operations of the PDT apparatus.

FIG. 5 is a flowchart showing operations of the PDT apparatus.

The operations of the PDT apparatus 1 will be described in the following order of (1) to (6).

(1) Preparation for PDT (Step S101 to Step S103)

(2) Pharmaceutical-concentration-monitoring operation (Step S104 to Step S105)

In the pharmaceutical-concentration-monitoring operation, the light source 110 outputs an excitation light with a first intensity, and the controller 150 constantly calculates the pharmaceutical concentration based on fluorescence intensity detected by the detection unit 130, and determines whether to additionally administer pharmaceutical or not based on the calculated pharmaceutical concentration.

(3) Contact-monitoring operation (Step S106 to Step S108)

In the contact-monitoring operation, the light source 110 outputs the excitation light with the first intensity, and the controller 150 determines the contact state of the laser catheter 300 with respect to a tissue inner wall based on fluorescence intensity detected by the detection unit 130, and calculates excitation-light-irradiation protocols (intensity, time, and the like).

(4) Foreign-substance/breakage-monitoring operation (Step S109 to Step S112)

In the foreign-substance/breakage-monitoring operation, the light source 110 outputs the excitation light with a second intensity, and the controller 150 determines whether a foreign substance adheres to the tip of the laser catheter 300 for some reason or not and further determines whether a breakage occurs in the vicinity of the tip of the laser catheter 300 or not, during laser-irradiation at appropriate therapy protocols, based on the fluorescence intensity detected by the detection unit 130.

(5) Cytocidal-effect-determining operation (Step S113)

In the cytocidal-effect-determining operation, the light source 110 outputs the excitation light with the second intensity, and the controller 150 determines whether there is a cytocidal effect on a tissue, on which the excitation light is being irradiated, or not based on the fluorescence intensity detected by the detection unit 130.

(6) Electric-conduction-block-formation determining operation (Step S114 to Step S117)

An electric-conduction block is, as described above, a block in which cardiac-muscle tissues surrounding a hyperexcited site are necrotized, and in which conduction of electrical pulses from the hyperexcited site to the left atrium is blocked. Here, it is determined whether an electric-conduction block is formed or not by calculating, by the controller, temporal-change data of fluorescence intensity used in the cytocidal-effect-determining operation (Step S113), and electrocardiographic-wave data. In some cases, the laser catheter may be relocated in the electric-conduction block, the intensity of the light source 110 may be changed to the first intensity, and the similar process may be performed, to thereby determine whether an electric-conduction block is formed or not.

[(1) Preparation for PDT]

Figure 6:
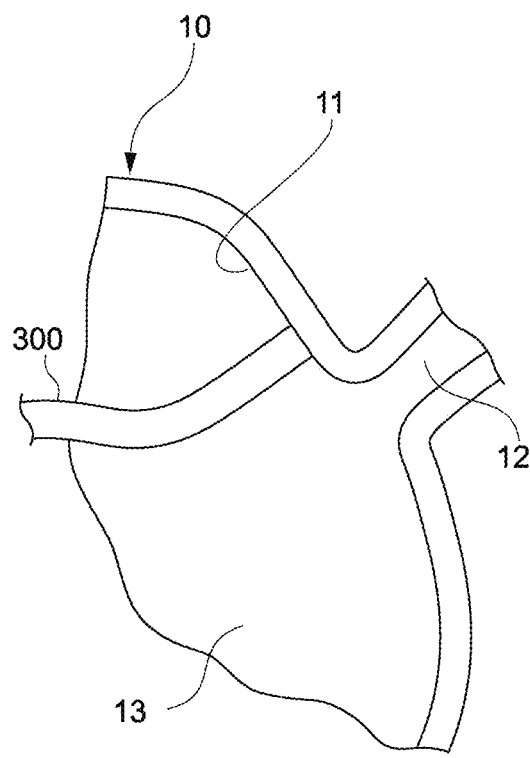
FIG. 6 A schematic diagram showing the laser catheter inserted in a left atrium.

FIG. 6 is a schematic diagram showing a laser catheter inserted in a left atrium.

First, a practitioner such as a doctor inserts the laser catheter 300 in the heart 10 via a femoral vein or a jugular vein of the patient 2. The tip portion of the laser catheter 300 is disposed in the vicinity of a pulmonary vein 12 of an inner wall of a the cardiac-muscle tissue 11 of the left atrium 13 (Step S101).

Subsequently, with reference to various referential data (Step S102), the practitioner administers photo-sensitive pharmaceutical to the patient 2 (Step S103). Here, the case where a dose of photo-sensitive pharmaceutical necessary for therapy is administered to the patient 2 at one time by intravenous injection will be described. The administered photo-sensitive pharmaceutical is diffused in blood and absorbed in a tissue.

[(2) Pharmaceutical-Concentration-Monitoring Operation]

Subsequently, the pharmaceutical-concentration-monitoring operation is performed.

First, the practitioner operates the operating unit 180, and inputs an excitation-light-output instruction with the low-power first intensity to the controller 150. The controller 150 obtains the excitation-light-output instruction, and then outputs the excitation-light-output instruction with the first intensity, to the light source 110. The light source 110 obtains the excitation-light-output instruction from the controller 150, and then outputs the excitation light with the first intensity. Tissues and blood are irradiated with the excitation light output from the light source 110 via the optical system 120 and the laser catheter 300. The photo-sensitive pharmaceutical, which is absorbed in a tissue and blood, absorbs the excitation light from the laser catheter 300, and emits fluorescence. The optical system 120 extracts the fluorescence emitted from the photo-sensitive pharmaceutical via the laser catheter 300, and the fluorescence enters the detection unit 130. The detection unit 130 detects the entered fluorescence, and outputs the detected fluorescence intensity to the controller 150 as an electrical signal.

The controller 150 calculates the fluorescence intensity based on the electrical signal obtained from the detection unit 130. The controller 150 starts to record, in the storage 160, the temporal change of the fluorescence intensity as a log in which the calculated fluorescence intensity is in relation with time information obtained from a timing measurement unit (not shown.). The controller 150 creates display information of the temporal change of the fluorescence intensity based on the calculated fluorescence intensity and elapsed time after a criterion time such as an intravenous-injection start time, and outputs a display instruction including the created display information to the display unit 170. The display unit 170 obtains the display instruction from the controller 150, and then displays the temporal change of the fluorescence intensity on a display screen based on the display information included in the display instruction. For example, the display unit 170 displays the temporal change of the fluorescence intensity on the display screen in a graph form.

Here, an example of the graph showing the temporal change of the fluorescence intensity will be described.

Figure 7:
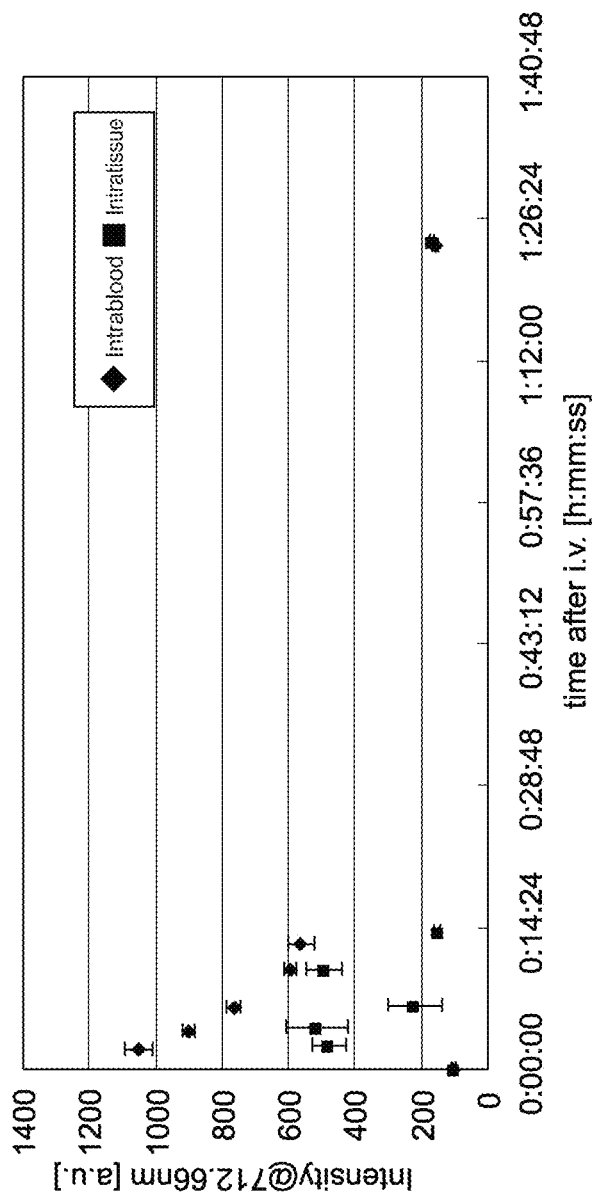
FIG. 7 A graph showing the temporal change of fluorescence intensity.

FIG. 7 is a graph showing a temporal change of fluorescence intensity.

FIG. 7 shows the temporal change of fluorescence intensity in the case where photo-sensitive pharmaceutical (Laserphyrin) is administered to a pig by intravenous injection (i.v.), and irradiation is performed with an excitation light, which is the same as the Q-band absorption spectrum of the pharmaceutical (semiconductor laser, emission wavelength with, for example 600 to 800 nm, preferably 660 to 680 nm, or more preferably 664 plus or minus 2, 400 µW). The tip portion of the laser catheter 300 is disposed in the right atrium of the pig.

The fluorescence intensity in blood monotonically decreases after the pharmaceutical administration. Meanwhile, the fluorescence intensity in a cardiac-muscle tissue increases for a predetermined time period after the pharmaceutical administration, and then decreases. Further, the fluorescence intensity in the blood is higher than the fluorescence intensity in the cardiac-muscle tissue.

Here, the relation between fluorescence intensity and pharmaceutical concentration will be described.

Figure 8:
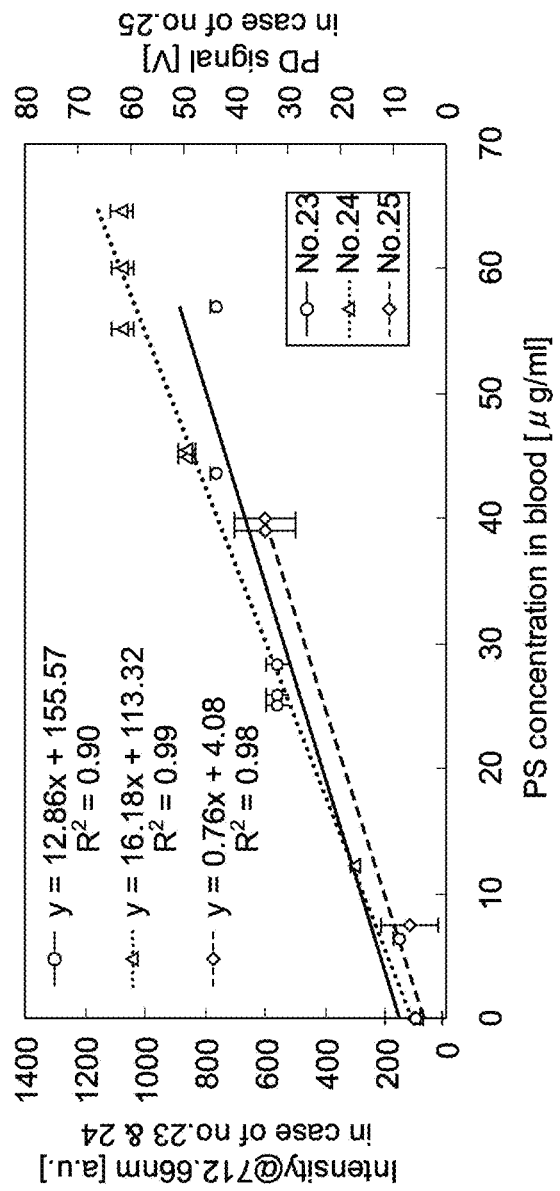
FIG. 8 A graph showing the correlation between the fluorescence intensity and pharmaceutical concentration.

FIG. 8 is a graph showing a correlation between fluorescence intensity and pharmaceutical concentration.

FIG. 8 shows a correlation between absolute value of pharmaceutical concentration (PS concentration) obtained by a blood collection method, and the fluorescence intensity in the case where blood is irradiated with the excitation light as shown in FIG. 7. The absolute value of pharmaceutical concentration is almost the same as the fluorescence intensity. That is, it is possible to monitor pharmaceutical concentration in real time based on the constantly-calculated fluorescence intensity.

The controller 150 calculates pharmaceutical concentration in a tissue and in blood based on calculated fluorescence intensity (Step S104). The controller 150 starts to record, in the storage 160, the temporal change of the pharmaceutical concentration as a log in which the calculated pharmaceutical concentration is in relation with time information obtained from a timing measurement unit (not shown.). Further, the controller 150 creates display information of the temporal change of the pharmaceutical concentration based on the calculated pharmaceutical concentration and elapsed time after a criterion time such as an intravenous-injection start time, and outputs a display instruction including the created display information to the display unit 170. The display unit 170 obtains the display instruction from the controller 150, and then displays the temporal change of the pharmaceutical concentration on a display screen based on the display information included in the display instruction. For example, the display unit 170 displays the temporal change of the pharmaceutical concentration on the display screen in a graph form.

Here, an example of a graph showing the temporal change of the pharmaceutical concentration will be described.

Figure 9:
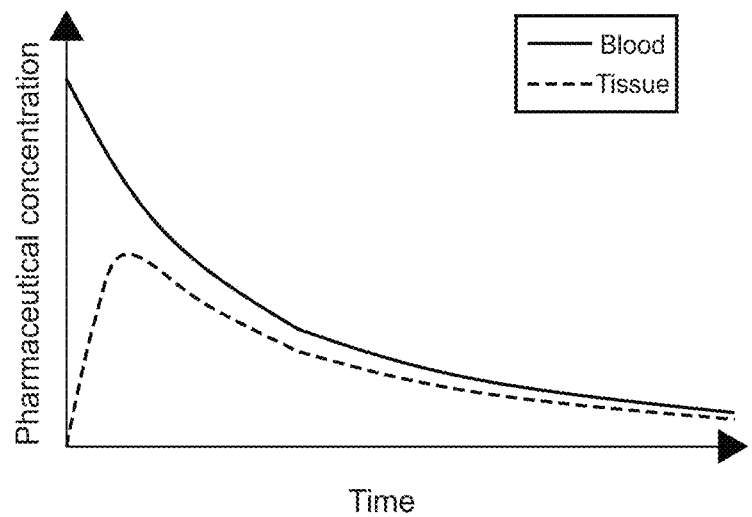
FIG. 9 A graph showing the temporal change of the pharmaceutical concentration.

FIG. 9 is a graph showing a temporal change of pharmaceutical concentration.

As described above, the fluorescence intensity in blood is higher than the fluorescence intensity in a cardiac-muscle tissue, and, in addition, the fluorescence intensity correlates with the pharmaceutical concentration. Therefore, similar to the temporal change of the fluorescence intensity in blood, the pharmaceutical concentration in blood monotonically decreases after the pharmaceutical administration. Meanwhile, similar to the temporal change of the fluorescence intensity in a tissue, the pharmaceutical concentration in a tissue increases for a predetermined time period after the pharmaceutical administration, and then decreases. Further, the pharmaceutical concentration in blood is higher in level than the pharmaceutical concentration in a tissue.

The controller 150 determines whether the calculated pharmaceutical concentration is equal to or more than a threshold (Step S105). If the controller 150 determines that the pharmaceutical concentration is equal to or more than the threshold, the controller 150 estimates that the pharmaceutical concentration reaches a necessary value, and moves to the contact-monitoring operation (Step S105, Yes). Meanwhile, if the controller 150 determines that the pharmaceutical concentration is less than the threshold, the controller 150 estimates that the pharmaceutical concentration fails to reach the necessary value, creates display information for prompting to additionally administer the pharmaceutical, and outputs the display instruction including the created display information to the display unit 170. The display unit 170 obtains the display instruction from the controller 150, and then displays, based on the display information including the display instruction, information prompting the practitioner to additionally administer the photo-sensitive pharmaceutical (Step S105, No).

Note that, because the fluorescence intensity correlates with the pharmaceutical concentration, if the display unit 170 displays the fluorescence intensity on the display screen, a practitioner such as a doctor may estimate the pharmaceutical concentration based on the fluorescence intensity, even if the controller 150 does not calculate the pharmaceutical concentration.

Meanwhile, in general, as a method of monitoring the pharmaceutical concentration change in blood, there is known a method in which absorbance of blood, which is collected at regular time intervals after pharmaceutical administration, is measured. However, in this method, the plot number is limited because the collectable blood volume is limited, and in addition, it is not possible to measure the concentration in real time.

Alternatively, there is known a method in which a bypass pathway is prepared outside of a body, blood passing through the pathway is irradiated with light, and fluorescence intensity is observed, to thereby monitor the pharmaceutical concentration change. However, it is necessary to pay attention to hygiene in this method.

Further, as a method of monitoring pharmaceutical concentration in a tissue, there is known a method in which part of carbon in pharmaceutical is transformed into isotope, the isotope is simultaneously administered, and pharmaceutical concentration in each tissue is monitored based on a radiation quantity (CANCER RESEARCH 50. 3985-3990, Jul. 1, 1990, Tissue Distribution and Photosensitizing Properties of Mono-L-aspartyl Chlorin e6 in a Mouse Tumor Model, Charles J. Corner and Angela Ferrario). However, this method involves radiation exposure problems, and involves a problem in that only a concentration may be monitored macroscopically.

To the contrary, according to the pharmaceutical-concentration-monitoring operation of this embodiment, by calculating the temporal change of fluorescence intensity, the temporal change of pharmaceutical concentration, which correlates with fluorescence intensity, may be calculated. Therefore the pharmaceutical concentration in a tissue and blood may be monitored in real time. Further, the pharmaceutical-concentration-monitoring operation of this embodiment is less invasive than the conventional monitoring method, and is capable of monitoring temporal changes of pharmaceutical concentration stably and reproducibly. Further, because the temporal change of pharmaceutical concentration is monitored via a catheter by using the excitation light from the light source 110 of the PDT apparatus 1, it is not necessary to additionally provide a pharmaceutical concentration detecting apparatus, to thereby enable a low-cost and space-saving apparatus. Further, because the pharmaceutical concentration may be monitored in real time, determination of additional pharmaceutical administration may be assisted in real time.

Further, the pharmaceutical-concentration-monitoring operation of this embodiment may be performed not only in PDT but also in therapy or diagnosis using a pharmaceutical, which absorbs an excitation light and emits fluorescence. In therapy or diagnosis using a pharmaceutical, it is important to grasp a pharmaceutical dynamic state (pharmaceutical delivery). According to the pharmaceutical-concentration-monitoring operation of this embodiment, pharmaceutical concentration in an intended tissue may be measured microscopically via a catheter in real time, and dynamic states of various pharmaceuticals may be grasped. Further, because minimally-invasive monitoring is enabled, the pharmaceutical-concentration-monitoring operation of this embodiment has a great advantage and is suitable for practical use. Further, the pharmaceutical-concentration-monitoring operation of this embodiment may be performed in a system (DDS, Drug Delivery System) in which pharmaceutical is delivered to only a certain location, and is useful to estimate whether pharmaceutical reaches actually and locally.

[(3) Contact-Monitoring Operation]

Subsequently, the contact-monitoring operation is performed.

Figure 10:
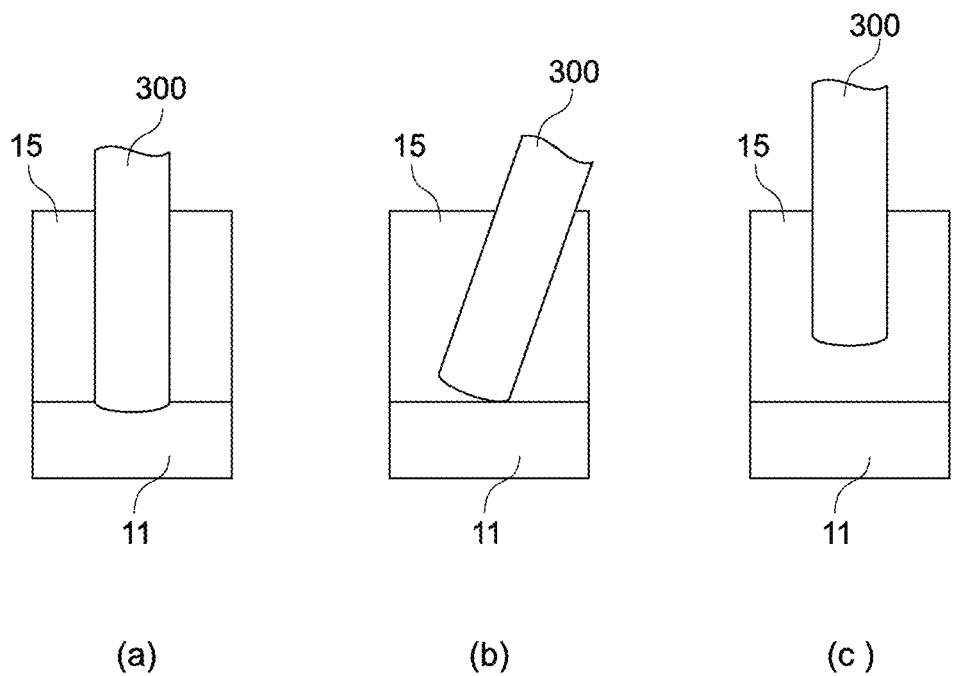
FIG. 10 Schematic diagrams each showing a contact state of the laser catheter.

FIG. 10 are schematic diagrams showing contact states of the laser catheter.

The laser catheter 300 is preferably disposed such that the tip portion as a light-emitting portion contacts the inner wall of the cardiac-muscle tissue 11 upright (see FIG. 10(a), hereinafter referred to as "upright-contact state".). This state is preferable so as to remove intraatrial blood 15 from the tip portion of the laser catheter 300, and to prevent activation of photo-sensitive pharmaceutical in the intraatrial blood 15. Further, this state is preferable so as to selectively activate photo-sensitive pharmaceutical absorbed in a tissue when the tip portion of the laser catheter 300 directly contacts a tissue.

However, it is difficult to recognize the precise contact state of the tip portion of the laser catheter 300 radiographically or tactually. Because of this, actually, it is not always true that the tip portion of the laser catheter 300 is in the upright-contact state with respect to a tissue. The blood 15 may exist between the tip portion of the laser catheter 300 and a tissue, and the tip portion may be in the blood (see FIG. 10(c), hereinafter referred to as "non-contact state".). Alternatively, the tip portion of the laser catheter 300 may contact a tissue in a slanting direction, and the blood 15 may partially exist in a gap between the tip portion and the tissue (see FIG. 10(b), hereinafter referred to as "slanting-contact state".).

In the contact-monitoring operation, such contact states of the tip portion of the laser catheter 300, that is, the contact states and the non-contact state, are monitored, the contact angle (upright-contact state, slanting-contact state) in the case of the contact states is monitored, and the like. Note that, in this specification, the "contact angle" not only means a narrowly-defined angular value, but also means a widely-defined contact angle, in which the contact state of the tip portion of the laser catheter 300 with respect to a tissue is upright or slanting.

Continuously, the light source 110 outputs the excitation light with the first intensity to the optical system 120, the controller 150 calculates fluorescence intensity and pharmaceutical concentration, and the display unit 170 displays the temporal change of fluorescence intensity on the display screen. For example, the display unit 170 displays the temporal change of fluorescence intensity on the display screen as a graph.

Here, an example of a graph showing the temporal change of fluorescence intensity will be described.

Figure 11:
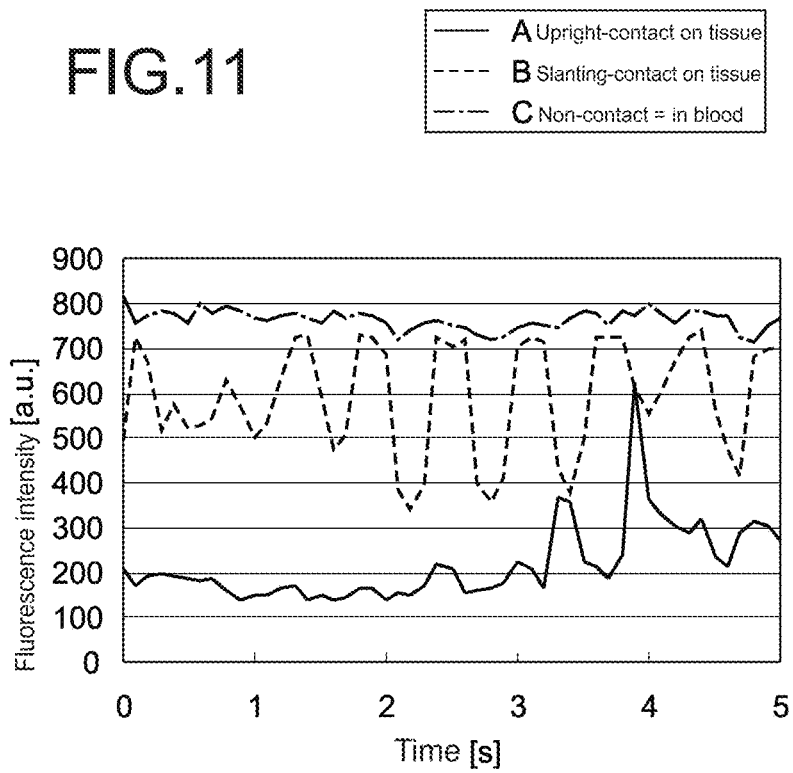
FIG. 11 A graph showing the temporal change of the fluorescence intensity.

FIG. 11 is a graph showing the temporal change of fluorescence intensity.

FIG. 11 is a graph showing the temporal change of fluorescence intensity under the condition same as FIG. 7. In the graph, the line A shows low fluorescence intensity, the line C shows high fluorescence intensity, and the line B fluctuates between the fluorescence intensity of the line A and the fluorescence intensity of the line C.

Note that, in FIG. 11, in order to make the description clear, the temporal change of fluorescence intensity in the case where the tip portion of the laser catheter 300 is in the upright-contact state, the temporal change of fluorescence intensity in the case where the tip portion of the laser catheter 300 is in the slanting-contact state, and the temporal change of fluorescence intensity in the case where the tip portion of the laser catheter 300 is in the non-contact state are shown in one graph. However, actually, one of them is displayed according to the contact state of the tip portion of the laser catheter 300.

The line A will be reviewed. Here, as shown in FIG. 7, the fluorescence intensity in a tissue is smaller than the fluorescence intensity in blood. Therefore, it is thought that the line A shows the fluorescence intensity in the case where the laser catheter 300 irradiates a tissue with the excitation light. So, in the case where the fluorescence intensity of the line A is calculated, it is thought that the fluorescence intensity in a tissue is reflected in the result because the tip portion of the laser catheter 300 is in the upright-contact state with respect to a tissue.

The line C will be reviewed. Here, as shown in FIG. 7, the fluorescence intensity in blood is larger than the fluorescence intensity in a tissue. Therefore, it is thought that the line C shows the fluorescence intensity in the case where the laser catheter 300 irradiates blood with the excitation light. So, in the case where the fluorescence intensity of the line C is calculated, it is thought that the fluorescence intensity in blood is reflected in the result because the tip portion of the laser catheter 300 is in the non-contact state with respect to a tissue.

The line B will be reviewed. Because the line B is between the fluorescence intensity of the line A and the fluorescence intensity of the line C, it is thought that the tip portion of the laser catheter 300 is in the slanting-contact state with respect to a tissue. Further, because a contact-target object of the tip portion of the laser catheter 300 is a moving cardiac-muscle tissue, the laser catheter 300 follows the movement of the tissue to thereby move. As a result, in the case where the tip portion of the laser catheter 300 contacts a tissue in a slanting manner, it is likely that the blood volume between the tip portion of the laser catheter 300 and a tissue changes during measurement. In addition, the blood-flow volume in a cardiac-muscle tissue changes and the intraatrial blood-flow volume changes because of heartbeat. Affected by them, the fluctuation of the fluorescence intensity of the line B is larger than the line A and the line C.

Further, in the case where the tip portion of the laser catheter 300 contacts a tissue in any state (upright-contact state, slanting-contact state), the laser catheter 300 may be affected by the movement of the cardiac-muscle tissue. That is, the contact state of the tip portion of the laser catheter 300 fluctuates between the contact states (upright-contact state, slanting-contact state) and the non-contact state. In this case, the fluorescence intensity fluctuates largely. Therefore, it is determined whether the laser catheter 300 follows the movement of a cardiac-muscle tissue or not based on fluctuation of the fluorescence intensity shown in a waveform. For example, in the line A of the graph, the high fluorescence intensity after four seconds after pharmaceutical administration and in the vicinity thereof shows that the tip portion of the laser catheter 300 momentarily moves from the upright-contact state to the non-contact state and returns to the upright-contact state again.

Based on the calculated fluorescence intensity, the controller 150 determines the contact state of the tip portion of the laser catheter 300 (contact/non-contact states, contact angle in case of contact state) (Step S106).

Specifically, in the case where the controller 150 determines that the calculated fluorescence intensity is equal to or larger than a first threshold, the controller 150 determines the non-contact state (line C). In the case where the controller 150 determines that the minimum value of the fluorescence intensity is equal to or smaller than a second threshold, which is smaller than the first threshold, the controller 150 determines the upright-contact state (line A). In the case where the controller 150 determines that the fluorescence intensity periodically fluctuates between the first threshold and the second threshold, the controller 150 determines the slanting-contact state (line B).

The controller 150 informs the practitioner the determined contact state by using the display unit 170. Specifically, when the controller 150 determines the slanting-contact state or the non-contact state, the controller 150 creates display information for prompting to change the contact state of the tip portion of the laser catheter 300, and outputs a display instruction including the created display information to the display unit 170. The display unit 170 obtains the display instruction from the controller 150, and then displays information for prompting a practitioner to change the contact state of the tip portion of the laser catheter 300 based on the display information in the display instruction (Step S107). The practitioner operates a handpiece or the like (not shown.) provided on the laser catheter 300, to thereby change the contact state of the tip portion of the laser catheter 300 with respect to a tissue.

The controller 150 continuously calculates fluorescence intensity and pharmaceutical concentration. The controller 150 refers to fluorescence intensity and pharmaceutical concentration stored in the storage 160. The controller 150 calculates the blood volume in the gap between the tip portion of the laser catheter 300 and a tissue based on the referred fluorescence intensity. The controller 150 calculates excitation-light-irradiation protocols during the therapy, that is, the second intensity of the excitation light, the irradiation time, and the like, based on the calculated blood volume and the referred pharmaceutical concentration (Step S108).

For example, in the case where the tip portion of the laser catheter 300 is in the slanting-contact state or the non-contact state and where blood exists in the gap, the loss of the excitation light (excitation light which does not reach tissue) is considered based on the blood volume, and the excitation-light-irradiation protocols are set, in which the second intensity is high and in which the irradiation time is long. The controller 150 calculates the excitation-light-irradiation protocols, creates display information on the irradiation protocols, and outputs display instruction including the created display information to the display unit 170. The display unit 170 obtains the display instruction from the controller 150, and then displays information on the excitation-light-irradiation protocols (second intensity, irradiation time) based on the display information in the display instruction.

As described above, the controller 150 calculates the pharmaceutical concentration and the blood volume based on the fluorescence intensity, and calculates the excitation-light-irradiation protocols based on the calculated pharmaceutical concentration and blood volume. That is, the controller 150 is capable of calculating the excitation-light-irradiation protocols based on the fluorescence intensity.

Note that, because the temporal change of fluorescence intensity differs depending on the contact state of the tip portion of the laser catheter 300, if the temporal change of fluorescence intensity is displayed on the display screen by the display unit 170, it is possible for a practitioner to estimate a contact state based on the temporal change of fluorescence intensity even if the controller 150 does not determine the contact state.

Meanwhile, in the field of circulatory disease, it is important to determine, in real time, the contact state of the tip portion of a catheter with respect to the intended tissue, the blood volume in a gap, and presence/absence of a foreign-substance/breakage in order to ensure safety and reliability. Further, in the case where the intended tissue is a movable target such as a cardiac-muscle tissue, it is necessary to determine the contact state in detail, in which a laser catheter follows the movement of the tissue, to reliably perform therapy. In the past, it is known to determine the contact state of a catheter by, for example, securing a transparent zone by removing blood, radioscopy, potential measurement (impedance measurement), potential mapping, temperature measurement, dynamic measurement (pressure, stress), reflected light measurement using a polychromatic light source, and the like. However, in the field of therapy and diagnosis via a catheter, it is difficult to determine the tip state of the catheter in blood, and a technique capable of determining the contact state in detail has not been developed yet. Each of the above-mentioned conventional methods is capable of determining the contact state roughly, and, in addition, has many problems as follows.

Securing a transparent zone by removing blood is a method in which a blood flow is temporarily blocked by using a balloon, saline or the like is flowed from a catheter tip portion to thereby secure a transparent zone, and a contact state is observed by using an angioscope. However, this method may lead to a peripheral-vessel-ischemia state.

With radioscopy, because of lacking accuracy, it is difficult to determine the distance of a gap between a catheter and a tissue, and the blood volume in the gap between the catheter and the intended tissue. Further, in the case of a moving tissue, it is not clear that the tip of a catheter follows the movement. As a result, the tip of a catheter may break blood (in case of intracardiac therapy) or blood-vessel wall (in case of intravascular therapy). Further, the amount of energy input in an intended tissue decreases below an estimated amount, and an enough therapeutic effect may not be achieved. Further, the biggest problem is that only a doctor, who has a knowledge of anatomy and is well-experienced (tactile impression when touching), can make a determination, subjectively (see Japanese Patent Application Laid-open No. 2007-525263).

Potential measurement (impedance measurement) is a method in which, since a cardiac-muscle tissue contracts and moves because of potential propagation, the contact state with respect to a cardiac-muscle tissue is determined by measuring the potential. However, in the case of performing an optical therapy, the tip portion of a catheter (contact portion with respect to cardiac-muscle tissue) is an optical window. Because of this, a potential-measured site may be provided on a portion other than the tip portion of the catheter. As a result, a light-irradiated site does not coincide with a potential-measured site, a diagnosis-target zone does not coincide with a therapy-target zone, and the therapy may not be performed precisely. Further, an electrode area is made smaller, and angle determination accuracy may thus be decreased. Further, because electric measurement is performed, there may be an effect of electromagnetic interference (see Japanese Patent Application Laid-open No. 2008-531170).

Potential mapping is a method in which potential measurement is three-dimensionally developed. However, a conventional apparatus lacks a resolution of determining a contact state in detail. Further, it takes time to perform determination, and an anthropogenic influence may occur because of an excessive contact pressure (see Japanese Patent Application Laid-open No. 2008-531170). Further, if a potential measuring catheter is displaced, a mapping image may not coincide with an actual position. Further, because electric measurement is performed, there may be an effect of electromagnetic interference (see Japanese Patent Application Laid-open No. 2008-531170).

Temperature measurement is a method in which, with respect to diseases including a vascular occlusion, an occlusion is determined by measuring temperature (see Japanese Patent Application Laid-open No. 2007-525263). However, this is a diagnostic method for only occlusions, and is not applicable to diseases including no occlusion zone such as, for example, atrial fibrillation and ventricular flutter. Further, unnecessary heat may be provided on a normal blood-vessel wall.

Dynamic measurement (pressure, stress) is a method in which a pressure sensor or a stress sensor is mounted on a catheter, and a contact-target object is determined (see Japanese Patent Application Laid-open No. 2009-542371, U.S. Pat. No. 6,696,808, US Patent Application Laid-open No. 2008/0009750, WIPO Publication No. 01/33165) However, the tip portion of the catheter may be larger, and there may be an effect of electromagnetic interference (see Japanese Patent Application Laid-open No. 2008-531170).

Reflected light measurement by using a polychromatic light source is a method in which absorption coefficients different from wavelengths are used. Specifically, by using a polychromatic light source, a tissue is determined based on reflection ratio differences of the respective wavelengths (see Japanese Patent No. 4261101). According to this method, although the blood volume between a catheter and a tissue may be estimated, an optical system may be complicated, an apparatus may be made larger, and the cost may be increased because a plurality of light sources are provided.

To the contrary, according to the contact-monitoring operation of this embodiment, by detecting fluorescence intensity, it is possible to determine the contact state with respect to an intended tissue and following-movements via a catheter in real time. This method is minimally invasive because it is not necessary to remove blood and the like. Further, because excitation-light-irradiation protocols may be calculated based on the determined contact state and the like, therapy and diagnosis may be assisted safely and reliably.

[(4) Foreign-Substance/Breakage-Monitoring Operation]

During the photodynamic therapy, the foreign-substance/breakage-monitoring operation is performed.

First, a practitioner refers to excitation-light-irradiation protocols displayed on the display unit 170, and operates the operating unit 180 to thereby input an excitation-light-output instruction with the high-power second intensity in the controller 150. The controller 150 obtains the excitation-lightoutput instruction, and then outputs the excitation-light-output instruction with the second intensity to the light source 110. The light source 110 obtains the excitation-light-output instruction from the controller 150, and then outputs the excitation light with the second intensity. A tissue is irradiated with the excitation light output from the light source 110 via the optical system 120 and the laser catheter 300, and photodynamic therapy is performed (Step S109).

Based on an electrical signal obtained from the detection unit 130, the controller 150 calculates fluorescence intensity. The controller 150 creates display information of the temporal change of the fluorescence intensity based on the calculated fluorescence intensity and elapsed time after a criterion time such as an intravenous-injection start time, and outputs a display instruction including the created display information to the display unit 170. The display unit 170 obtains the display instruction from the controller 150, and then displays the temporal change of the fluorescence intensity on a display screen based on the display information included in the display instruction.

The controller 150 determines whether the calculated fluorescence intensity is equal to or more than a threshold (Step S110). The threshold is, for example, a value equal to or more than the multiple of the normal fluorescence intensity.

FIG. 19 is a graph showing the relation between wavelength and fluorescence intensity.

FIG. 19 shows the relation between wavelength and fluorescence intensity of a laser catheter, which may contact a foreign substance or may be broken, and those of a normal laser catheter. It is understood that, in the case where the tip portion of a laser catheter contacts a foreign substance other than a living body tissue or is broken, the fluorescence intensity thereof is larger than the normal fluorescence intensity.

The controller 150 determines that the fluorescence intensity is equal to or more than the threshold, that is, determines that the fluorescence intensity is increased to equal to or more than the multiple of the previous fluorescence intensity such that the current fluorescence intensity ignores the previous fluorescence intensity, and then the controller 150 estimates that there is a foreign substance or a breakage (Step S110, Yes). If the controller 150 estimates that there is a foreign substance or a breakage, the controller 150 creates display information on generation of a foreign-substance/breakage to stop the excitation light irradiation, and outputs display instruction including the created display information to the display unit 170. The display information on generation of a foreign-substance/breakage includes information to stop the excitation light irradiation, to reset irradiation time, to reset an irradiation power, to prompt to check the laser catheter 300, and the like. When the display unit 170 obtains the display instruction from the controller 150, based on the display information in the display instruction, the display unit 170 displays information to stop the excitation light irradiation (Step S111) and information on generation of a foreign-substance/breakage (Step S112) to a practitioner.

Note that, in the case where the controller 150 detects abnormal intensity increase of an arbitrary wavelength other than the fluorescence wavelength (excitation light wavelength or the like), the controller 150 estimates that there is a foreign substance or a breakage (Step S110, Yes), and may perform the similar processing (Step S111, Step S112).

Meanwhile, in the case where the controller 150 does not determine that the fluorescence intensity is equal to or more than the threshold within a predetermined time period, the controller 150 estimates that there is no foreign substance or breakage, and moves to the cytocidal-effect-determining operation (Step S110, No).

Note that, because generation of a foreign substance or a breakage is estimated when the fluorescence intensity exceeds a predetermined threshold, if the display unit 170 displays the fluorescence intensity on the display screen, a practitioner may estimate generation of a foreign substance or a breakage based on the fluorescence intensity, even if the controller 150 does not estimate generation of a foreign substance or a breakage.

Further, in the case where a plurality of catheters are disposed in a cardiac cavity in addition to the laser catheter 300, the laser catheter 300 may contact another catheter. For example, if the laser catheter 300 emits a light in the state where the laser catheter 300 contacts another catheter disposed in a cardiac cavity, both of the catheters may lose their functions. If a practitioner is keep on emitting an excitation light without noticing the abnormal situation of the tip portion of the laser catheter 300, the tip portion of the laser catheter 300 may generate heat to thereby be in danger of thermally damaging a living body. Further, a catheter being contacted may lose its function.

According to the foreign-substance/breakage-monitoring operation of this embodiment, because a strong reflected light is measured when the catheter contacts any object other than a living body tissue, it is possible to estimate generation of a foreign-substance/breakage via a catheter in real time. Because of this, it is possible to prompt a practitioner to check the laser catheter 300, and thus it is possible to perform the therapy very safely without causing danger to a patient.

[(5) Cytocidal-Effect-Determining Operation]

Subsequently, the cytocidal-effect-determining operation is performed.

In photodynamic therapy, photo-sensitive pharmaceutical absorbed in a tissue absorbs the excitation light from the laser catheter 300 to gain energy, and changes from the ground state to the singlet excited state. Most of the energy changes from the singlet excited state to the triplet excited state because of intersystem crossing, but the rest part returns from the singlet state to the ground state, and emits fluorescence at this time. Further, when photo-sensitive pharmaceutical in the triplet excited state clashes triplet oxygen, the photo-sensitive pharmaceutical transfers energy to oxygen, and creates strong oxidizer singlet oxygen. The oxidizer breaks a tissue, and, in addition, breaks photo-sensitive pharmaceutical (bleaching). If the bleaching occurs, the effective pharmaceutical amount is decreased, and thus the fluorescence amount is also decreased. Therefore, decrease of the fluorescence amount indicates bleaching and a tissue injury amount. The optical system 120 extracts the fluorescence emitted from the photo-sensitive pharmaceutical via the laser catheter 300, and the fluorescence enters the detection unit 130. The detection unit 130 detects the fluorescence entered from the optical system 120, and outputs the intensity of the detected fluorescence to the controller 150 as an electrical signal.

Continuously, the light source 110 outputs the excitation light with the second intensity to the optical system 120, the controller 150 calculates the fluorescence intensity, and the display unit 170 displays the temporal change of fluorescence intensity on the display screen. For example, the display unit 170 displays the temporal change of fluorescence intensity on the display screen as a graph.

Here, an example of a graph showing the temporal change of fluorescence intensity will be described.

Figure 12:
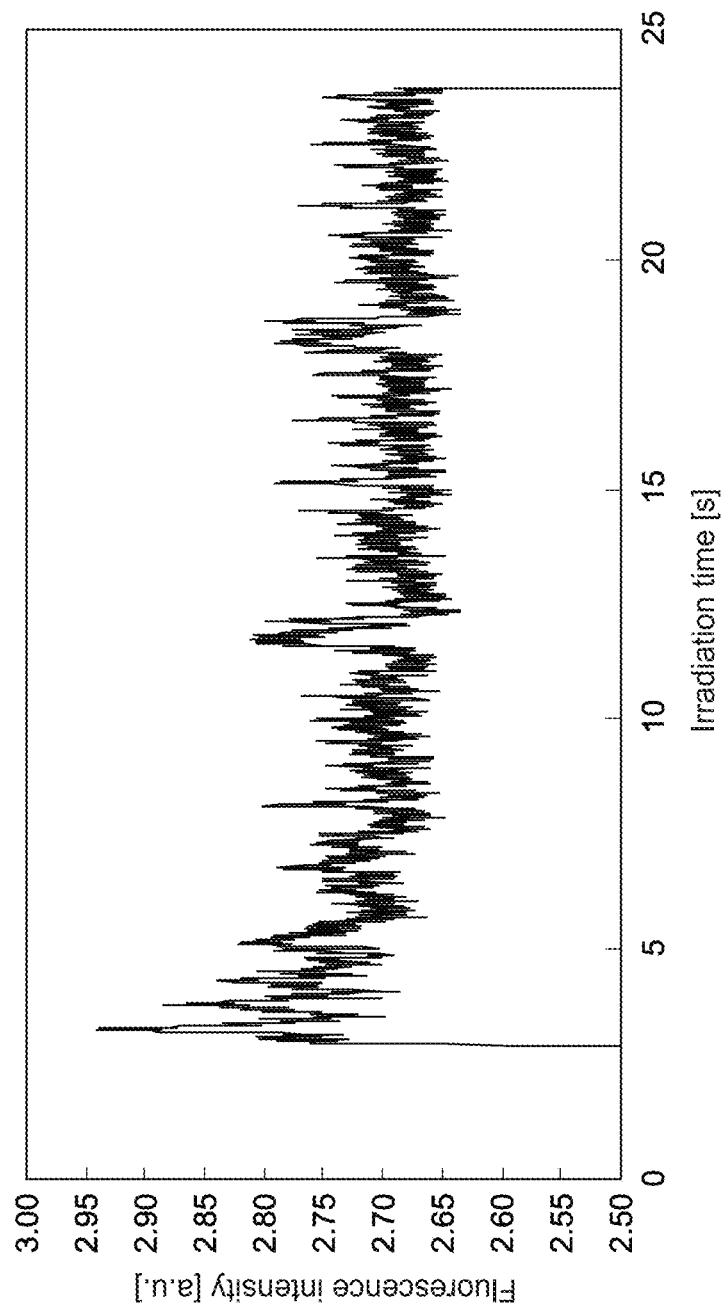
FIG. 12 Another graph showing the temporal change of the fluorescence intensity.

FIG. 12 is a graph showing the temporal change of fluorescence intensity.

FIG. 12 shows the temporal change of fluorescence intensity in the case where the excitation light is emitted for 20 seconds after 20 minutes pass after photo-sensitive pharmaceutical is administered in a pig by intravenous-injection. Since decrease of a fluorescence amount indicates bleaching and a tissue injury amount as described above, by displaying an attenuation curve of the fluorescence intensity, the PDT process level may be displayed in real time.

The controller 150 determines whether the calculated fluorescence intensity is attenuated below a threshold (Step S113). If the controller 150 determines that the fluorescence intensity is attenuated below the threshold, the controller 150 estimates that there is a cytocidal effect on a tissue irradiated with the excitation light (Step S113, Yes). Then, the controller 150 creates display information on an index of a cytocidal effect, and outputs a display instruction including the created display information to the display unit 170. The display unit 170 obtains the display instruction from the controller 150, and then displays information on an index of a cytocidal effect for a practitioner based on the display information in the display instruction. The practitioner refers to the information on an index of a cytocidal effect displayed on the display unit 170, and moves to the electric-conduction-block-formation determining operation.

Meanwhile, if the controller 150 does not determine that the fluorescence intensity is decreased below the threshold within a predetermined time period, the controller 150 creates display information to prompt to extend the excitation light irradiation and to reset the light intensity based on the calculated fluorescence intensity, and outputs display instruction including the created display information to the display unit 170 (Step S113, No). When the display unit 170 obtains the display instruction from the controller 150, the display unit 170 displays information to prompt a practitioner to extend the excitation light irradiation and to reset the light intensity based on the display information in the display instruction. After a predetermined time period passes after outputting the display instruction, the controller 150 moves to the operation of Step S108.

Note that, because generation of a cytocidal effect is estimated when the fluorescence intensity is attenuated below a predetermined threshold, if the display unit 170 displays the fluorescence intensity on the display screen, a practitioner may estimate whether there is a cytocidal effect or not based on the fluorescence intensity, even if the controller 150 does not estimate whether there is a cytocidal effect or not.

According to the cytocidal-effect-determining operation of this embodiment, based on fluorescence intensity correlated with pharmaceutical concentration, it is possible to measure injury in a cardiomyocyte, which progresses in a tissue irradiated with the excitation light, that is, to measure a therapeutic effect, via a catheter in real time, and thus the therapy is performed reliably.

[(6) Electric-Conduction-Block-Formation Determining Operation]

Subsequently, the electric-conduction-block-formation determining operation is performed.

In the electric-conduction-block-formation determining operation, the fluorescence time-waveform used in the cytocidal effect determination is in synchronization with electrocardiogram (ECG. ECG obtaining method will be described later.). The controller 150 analyzes the phase difference between the ECG R-wave and the fluorescence peak intensity in the interval between R-waves to thereby determine whether an electric-conduction block is formed. In some cases, the laser catheter 300 may be relocated in an electric-conduction block (in dashed-dotted line of FIG. 13), the excitation light output may be changed to the first intensity, and the fluorescence time-waveform, which is measured in low power, may be in synchronization with ECG to thereby perform analysis. The procedure in the case of relocating a laser catheter for measurement is as follows.

First, a practitioner disposes the tip portion of the laser catheter 300 in an electric-conduction block (in dashed-dotted line of FIG. 13) or on an excitation-light-irradiated site. Then, the practitioner operates the operating unit 180 to thereby input an excitation-light-output instruction with the low-power first intensity to the controller 150. The controller 150 obtains the excitation-light-output instruction, and then outputs the excitation-light-output instruction with the first intensity to the light source 110. The light source 110 obtains the excitation-light-output instruction from the controller 150, and then outputs the excitation light with the first intensity. A tissue is irradiated with the excitation light output from the light source 110 via the optical system 120 and the laser catheter 300. Photo-sensitive pharmaceutical, which is absorbed in a tissue, absorbs the excitation light from the laser catheter 300, and emits fluorescence. The optical system 120 extracts the fluorescence emitted from the photo-sensitive pharmaceutical via the laser catheter 300, and the fluorescence enters the detection unit 130. The detection unit 130 detects the fluorescence entered from the optical system 120, and outputs the detected fluorescence intensity to the controller 150 as an electrical signal. The controller 150 calculates fluorescence intensity based on the obtained electrical signal.

Meanwhile, the electrocardiograph 140 obtains the electrocardiographic signal, and supplies the obtained electrocardiographic signal to the controller 150. The controller 150 creates display information based on the calculated fluorescence intensity and the obtained electrocardiographic signal, and outputs display instruction including the created display information to the display unit 170. The display unit 170 obtains the display instruction from the controller 150, and displays the correlation between the fluorescence intensity and the electrocardiogram R-wave on the display screen based on the display information in the display instruction.

Here, the correlation between fluorescence intensity and ECG R-wave will be described.

Figure 14:
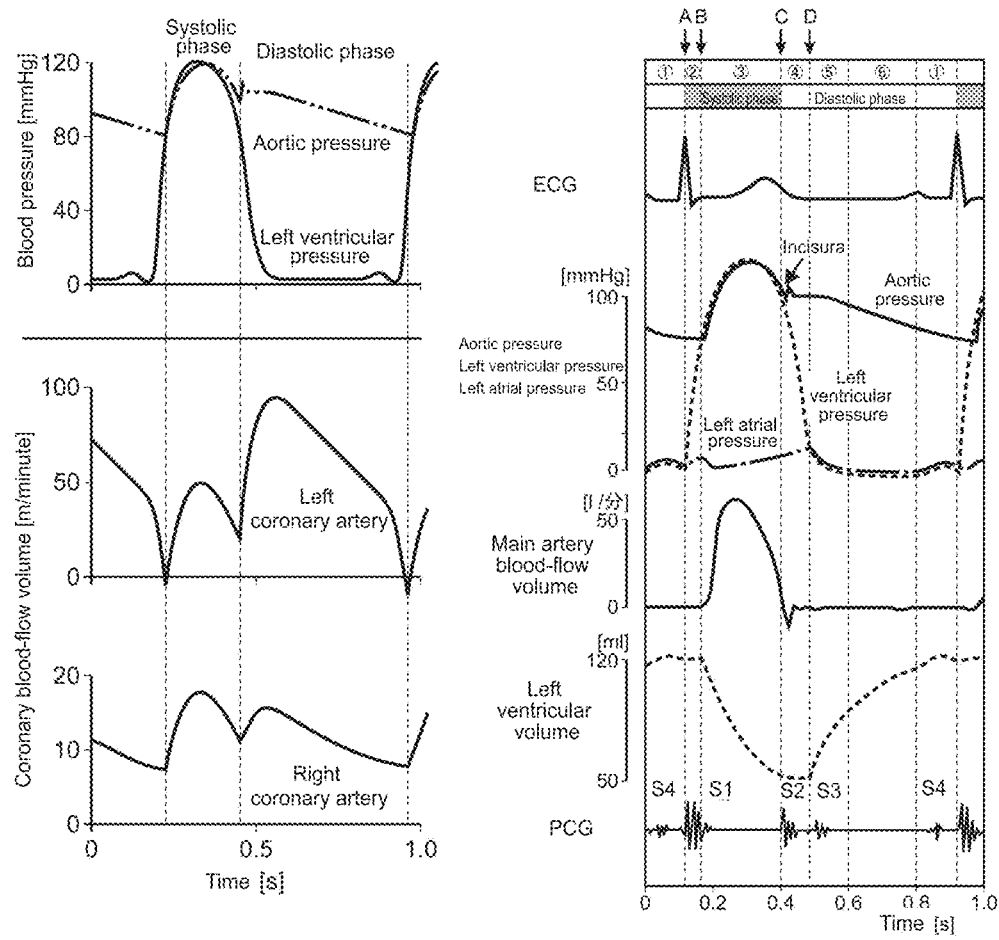
FIG. 14 A diagram showing the relation of ECG, intracardiac pressure, and coronary blood-flow volume, which is dominant in the blood-flow volume in a cardiac-muscle tissue.

FIG. 14 is a diagram showing the relation of ECG, intracardiac pressure, and coronary blood-flow volume, which is dominant in the blood-flow volume in a cardiac-muscle tissue, and being a prerequisite knowledge described in "Essential Anatomy and Physiology (Essensharu Kaibo Seirigaku)" (Gakken Medical Shujunsha Co., Ltd., 2001), which is effective in the following description.

As shown in FIG. 14, the temporal change of the intracardiac blood-flow volume is different from the blood-flow volume in a cardiac-muscle tissue. While the intracardiac blood-flow volume has a peak at the time when it coincides with R-wave, the blood-flow volume in a right-sided cardiac-muscle tissue has a first peak at the time when about 200 ms pass after R-wave, and a second peak at the time when about 400 ms pass after R-wave.

Figure 15:
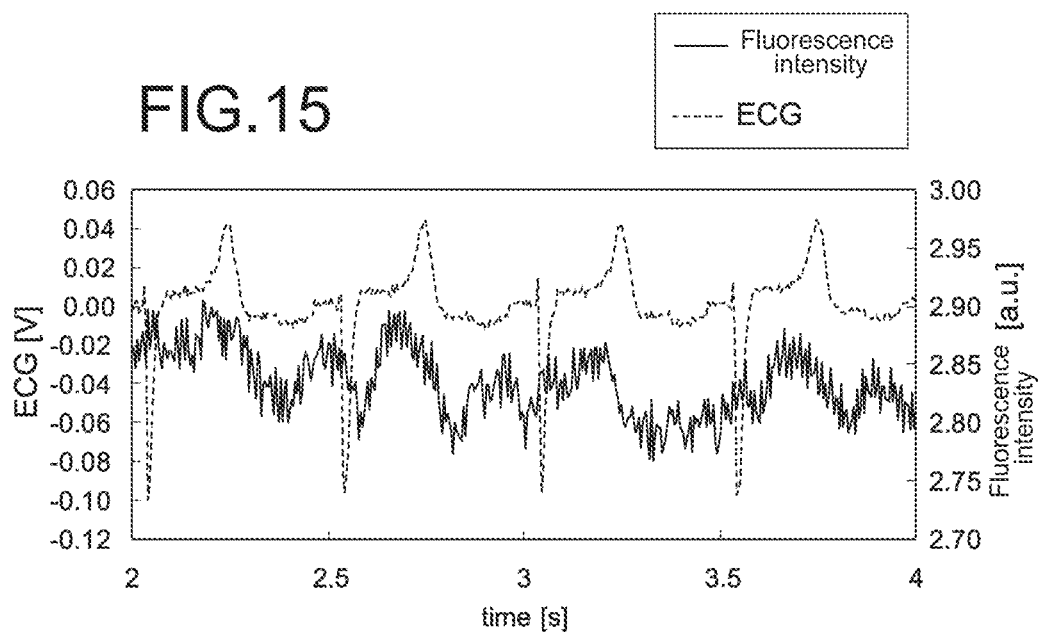
FIG. 15 A diagram showing the correlation between fluorescence intensity and R-wave when the laser catheter is in the upright-contact state.

FIG. 15 is a diagram showing the correlation between fluorescence intensity and R-wave when the laser catheter is in the upright-contact state.

The correlation between fluorescence intensity (for example, irradiation power of 900 mW) and R-wave when the tip portion of the laser catheter 300 is in the upright-contact state will be described. In the upright-contact state, fluorescence peaks are observed after 100 ms pass after R-wave and after 400 ms pass after R-wave. Note that, in the case where the catheter is disposed left-sided, the fluorescence intensity changes in proportion to the left coronary blood-flow volume of FIG. 14. A ventricle contracts when R-wave appears, and blood is supplied to a whole body (including cardiac-muscle tissue). Since blood includes photo-sensitive pharmaceutical, the fluorescence intensity in a cardiac-muscle tissue is highest when blood is supplied to blood vessels of a cardiac muscle. As a result, the peak of fluorescence intensity appears for a predetermined time period after appearance of R-wave.

Figure 16:
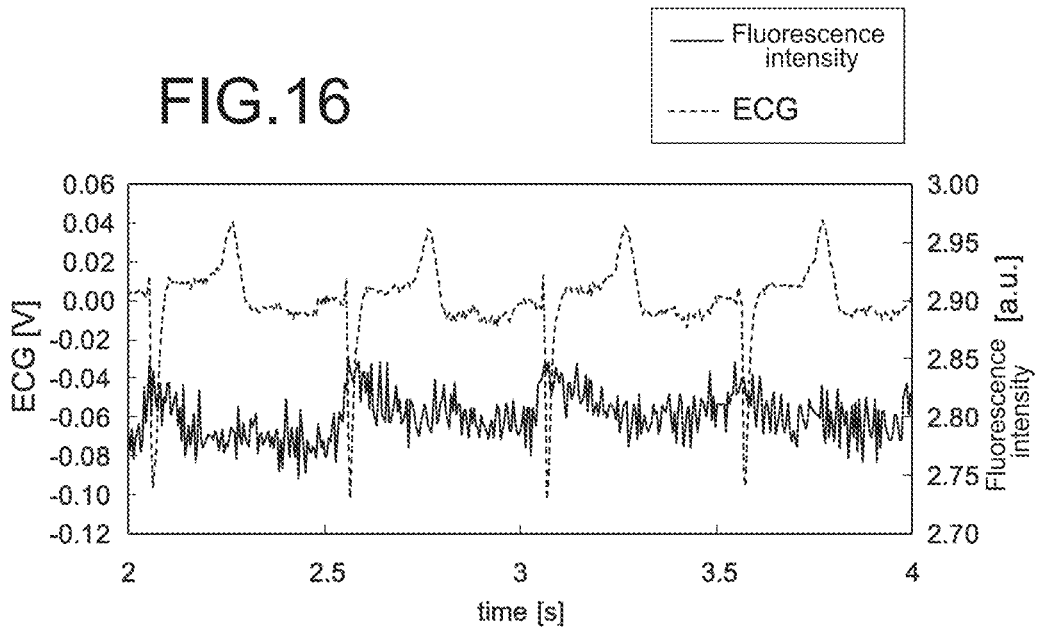
FIG. 16 A diagram showing the correlation between fluorescence intensity and R-wave when the laser catheter is in the slanting-contact state.

FIG. 16 is a diagram showing the correlation between fluorescence intensity and R-wave when the laser catheter is in the slanting-contact state.

The correlation between fluorescence intensity (for example, irradiation power of 900 mW) and R-wave when the tip portion of the laser catheter 300 is in the slanting-contact state will be described. In the slanting-contact state, because blood exists in a gap and the intracardiac blood-flow volume is dominant, the fluorescence intensity peak coincides with R-wave.

As described above, the phase difference between R-wave and fluorescence intensity peak in the upright-contact state is obviously different from the phase difference between R-wave and fluorescence intensity peak in the slanting-contact state, and the phase difference is constant if the contact state is maintained.

In view of this, the controller 150 determines whether the phase difference between fluorescence intensity and R-wave is constant based on the calculated fluorescence intensity and the obtained electrocardiographic signal, to thereby determine whether an electric-conduction block is formed or not (Step S114). If the controller 150 determines that the phase difference between fluorescence intensity and R-wave is constant, the controller 150 determines that an electric-conduction block is yet to be formed (Step S114, No), and causes the display unit 170 to display information to prompt a practitioner to stop the excitation light irradiation (Step S116) and to move the laser catheter 300 (Step S117). The practitioner refers to the information displayed on the display unit 170, stops excitation light irradiation once, and moves the laser catheter 300. Then, the processing of Step S104 and thereafter are performed again.

Figure 13:
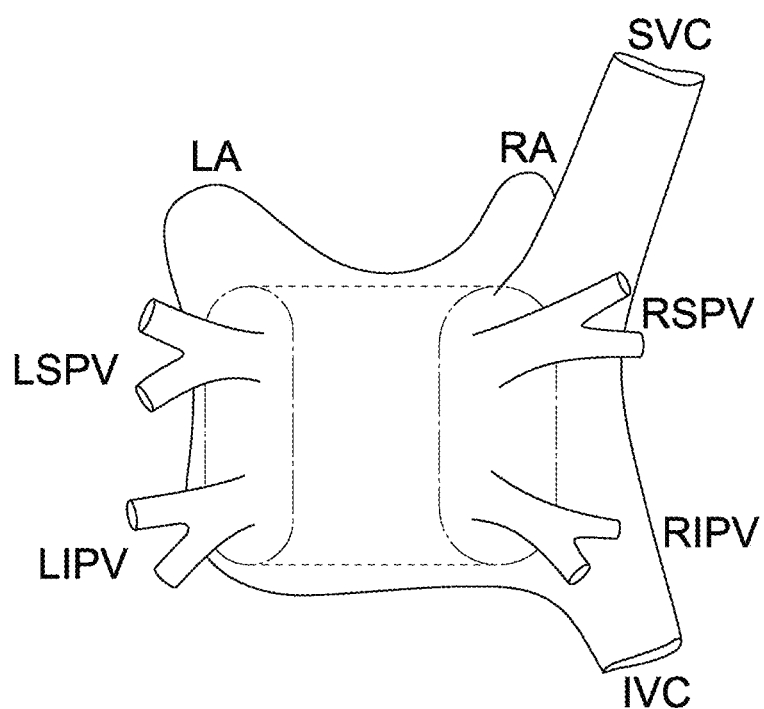
FIG. 13 A schematic diagram showing a movement track of the laser catheter.

FIG. 13 is a schematic diagram showing a movement track of the laser catheter.

A practitioner moves the tip portion of the laser catheter 300 so as to surround a hyperexcited site in pulmonary veins (PV) (dashed-dotted line or dashed line in FIG. 13).

Meanwhile, if the controller 150 determines that the phase difference between fluorescence intensity is R-wave is not constant, the controller 150 determines that an electric-conduction block is formed (Step S114, Yes), creates a display instruction to prompt a practitioner to stop excitation light irradiation and to remove the laser catheter 300, and outputs a display instruction including the created display information to the display unit 170. When the display unit 170 obtains the display instruction from the controller 150, the display unit 170 displays information to prompt a practitioner to stop excitation light irradiation and to remove the laser catheter 300 on the display screen based on the display information in the display instruction, and stops the processing (Step S115).

Here, the principle, in which the controller 150 determines that an electric-conduction block is formed when the phase difference between fluorescence intensity and R-wave is not constant, will be described. When a cardiomyocyte injury progresses, the cardiomyocyte fails to conduct electricity, and thus the cardiomyocyte fails to contract by itself at time of heartbeat. An electric-conduction block, which is formed by the injured cardiomyocytes and has a box shape, fails to contract by itself, and moves such that the electric-conduction block follows the contraction movement of the adjacent cardiac-muscle tissue. As a result, the contact state of the tip portion of the laser catheter 300 is unstable and changes every second. As a result, the phase difference between fluorescence intensity and R-wave becomes unstable. In other words, the correlation between fluorescence intensity and R-wave moves backward and forward between the correlation shown in FIG. 15 and the correlation shown in FIG. 16.

In view of this, according to the electric-conduction-block-formation determining operation of this embodiment, it is possible to determine that an electric-conduction block is formed in real time based on the phase difference between fluorescence intensity and electrocardiogram R-wave.

Specifically, in the case where the peak of fluorescence intensity appears for a predetermined time period after appearance of R-wave, it can be determined that an electric-conduction block is yet to be formed, and that the tip portion of the laser catheter 300 is in the upright-contact state. In the case where the peak of fluorescence intensity and the R-wave appear substantially simultaneously, it can be determined that an electric-conduction block is yet to be formed, and that the tip portion of the laser catheter 300 is in the slanting-contact state. In the case where the phase difference between the peak of fluorescence intensity and R-wave is not constant, it can be determined that an electric-conduction block is formed.

Note that, because it can be determined that an electric-conduction block is formed in the case where the phase difference between fluorescence intensity and R-wave is not constant, if the display unit 170 displays the correlation between fluorescence intensity and R-wave on the display screen, a practitioner may estimate whether an electric-conduction block is formed or not based on the correlation between fluorescence intensity and R-wave, even if the controller 150 does not estimate whether an electric-conduction block is formed or not.

Second Embodiment

Next, a PDT apparatus according to another embodiment of the present invention will be described. In the following description, descriptions of configurations, functions, operations, and the like similar to those of the PDT apparatus 1 of the first embodiment will be omitted or simplified, and different points will mainly be described.

An optical system and a detection unit according to the second embodiment will be described.

[Structures of Optical System and Detection Unit]

Figure 17:
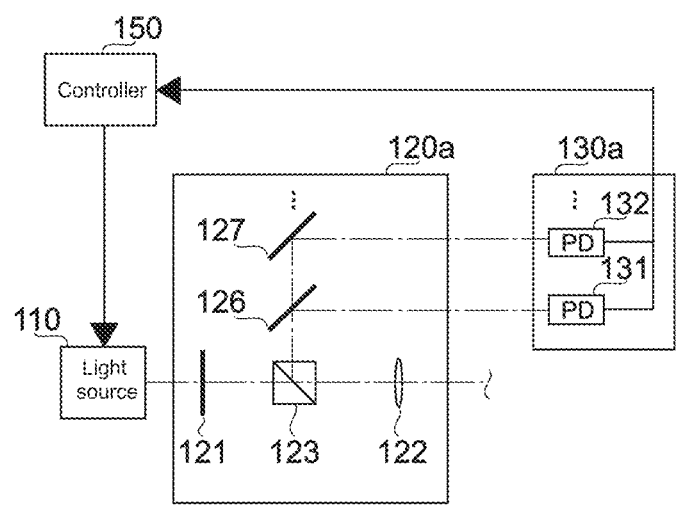
FIG. 17 A block diagram showing an optical system, a detection unit, and the like of a second embodiment of the present invention.

FIG. 17 is a block diagram showing an optical system, a detection unit, and the like of the second embodiment of the present invention.

An optical system 120a includes the short pass filter 121, the first lens 122, the PBS 123, a first dichroic mirror (hereinafter referred to as "DM".) 126, and a second DM 127.

A detection unit 130a includes a first photodiode (hereinafter referred to as "PD".) 131, and a second PD 132.

The first DM 126 reflects light having a certain wavelength out of the light entered from the PBS 123, and causes the light having the other wavelengths to pass through. In this manner, the first DM 126 reflects part of fluorescence from the laser catheter 300, and allows the fluorescence having the other wavelengths from the laser catheter 300 and specular reflection light to pass thorough. The fluorescence, which has reflected off the first DM 126, enters the first PD 131.

The first PD 131 detects the fluorescence entered from the first DM 126. The first PD 131 outputs the detected fluorescence intensity to the controller 150 as an electrical signal.

The second DM 127 reflects light having a certain wavelength out of the light which has passed through the first DM 126, and causes the light having the other wavelengths to pass through. In this manner, the second DM 127 reflects part of fluorescence, which has passed through the first DM 126, and allows the fluorescence having the other wavelengths and specular reflection light to pass thorough. The fluorescence, which has reflected off the second DM 127, enters the second PD 132.

The second PD 132 detects the fluorescence entered from the second DM 127. The second PD 132 outputs the detected fluorescence intensity to the controller 150 as an electrical signal.

Note that the optical system 120a may further include DMs each having a structure similar to the structure of each of the first DM 126 and the second DM 127. In this manner, eventually, the plurality of DMs 126, 127 . . . reflect the fluorescence from the laser catheter 300, and the plurality of PDs 131, 132 . . . detect the fluorescence from the laser catheter 300. Then, the plurality of DMs 126, 127 . . . causes the specular reflection light to pass through.

Note that, as another embodiment, a pulse light source may be used as the light source 110, and the specular reflection light reflected off the fiber entrance edge may be temporally separated based on optical path length difference (about twice as long as length of laser catheter 300).

Third Embodiment

In the third embodiment, the contact-monitoring steps are performed based on the phase difference between the peak of fluorescence intensity, which is in the interval between R-waves, and R-wave.

In the electric-conduction-block-formation determining operation of the first embodiment, it is determined that an electric-conduction block is formed based on the phase difference between the peak of fluorescence intensity, which is in the interval between R-waves, and R-wave. This principle may be applied to the contact-monitoring operation.

The light source 110 outputs the excitation light with the first intensity to the optical system 120. The detection unit 130 detects the fluorescence entered from the optical system 120. The detection unit 130 outputs the detected fluorescence intensity to the controller 150 as an electrical signal. The controller 150 calculates fluorescence intensity based on the obtained electrical signal.

Meanwhile, the electrocardiograph 140 obtains an electrocardiographic signal, and supplies the obtained electrocardiographic signal to the controller 150. The controller 150 creates display information based on the calculated fluorescence intensity and the obtained electrocardiographic signal, and outputs display instruction including the created display information to the display unit 170. The display unit 170 obtains the display instruction from the controller 150, and displays the correlation between fluorescence intensity and electrocardiogram R-wave on the display screen based on the display information in the display instruction.

The controller 150 determines the contact state of the tip portion of the laser catheter 300 based on the calculated fluorescence intensity and the obtained electrocardiographic signal (Step S106). Specifically, if the controller 150 determines that the peak of fluorescence intensity appears for a predetermined time period after appearance of the R-wave, the controller 150 determines that the tip portion of the laser catheter 300 is in the upright-contact state. If the controller 150 determines that the peak of fluorescence intensity and the R-wave appear simultaneously, the controller 150 determines that the tip portion of the laser catheter 300 is in the slanting-contact state. Further, the blood volume between the tip portion of the laser catheter 300 and the inner wall of a tissue may be estimated based on fluorescence peak intensity.

Fourth Embodiment

According to the fourth embodiment, the contact-monitoring steps are performed by using autofluorescence spectrum differences. Note that, autofluorescence indicates light emitted from a tissue by itself, and does not mean fluorescence from a pharmaceutical. That is, the fourth embodiment describes a diagnostic method in which no pharmaceutical is used.

The light source 110 outputs an excitation light, with which the difference between the autofluorescence spectrum property of a cardiac-muscle tissue and the autofluorescence spectrum property of blood is determined easily. The detection unit 130 detects entered fluorescence. The detection unit 130 outputs the detected fluorescence intensity to the controller 150 as an electrical signal. The controller 150 calculates the fluorescence spectrum based on the obtained electrical signal. The controller 150 determines whether the calculated fluorescence spectrum shows the autofluorescence spectrum property of a cardiac-muscle tissue or the autofluorescence spectrum property of blood. The controller 150 compares the calculated fluorescence spectrum with the autofluorescence spectrum property of a cardiac-muscle tissue and the autofluorescence spectrum property of blood, and determines the contact state of the tip portion of the laser catheter 300 (Step S106). Specifically, if the controller 150 determines that the calculated fluorescence spectrum shows the autofluorescence spectrum property of a cardiac-muscle tissue, the controller 150 determines that the tip portion of the laser catheter 300 is in the upright-contact state. If the controller 150 determines that the calculated fluorescence spectrum shows the autofluorescence spectrum property of blood, the controller 150 determines that the tip portion of the laser catheter 300 is in the non-contact state. If the controller 150 determines that the calculated fluorescence spectrum does not show the each autofluorescence spectrum property, the controller 150 determines that the tip portion of the laser catheter 300 is in the slanting-contact state.

The contact-monitoring using the autofluorescence spectrum difference is also useful for laser-catheter contact-monitoring in the case of a therapy for a disease with a vascular occlusion (for example, arteriosclerotic disease or the like).

FIG. 18 are schematic diagrams each showing a contact state of a laser catheter in an intravascular lumen.

In a therapy for a disease with a vascular occlusion, it is desired to determine whether the tip portion of the laser catheter 300 contacts a vascular occlusion (atheromatous plaque) 21 in a blood vessel 20 (see FIG. 18(a)) or contacts a blood-vessel wall 22 (see FIG. 18(b)). Here, the composition ratio of collagen, elastin, lipid, and the like of a vascular occlusion is different from the composition ratio of a blood-vessel wall. Specifically, the composition ratio of a vascular occlusion (arteriosclerosis) is 70% of water, 5% of collagen, 6% of elastin, and 9% of lipid. The composition ratio of a blood vessel is 73% of water, 6.5% of collagen, 10.5% of elastin, and 1% of lipid. Because of this, the autofluorescence spectrum property of a vascular occlusion is different from the autofluorescence spectrum property of a blood-vessel wall. If a therapy-target site is irradiated with an excitation light, with which the property difference is determined easily, and fluorescence is measured, it is possible to determine whether the tip portion of the laser catheter 300 contacts the vascular occlusion 21 or the blood-vessel wall 22. Note that, because it can be determined whether there is an atheromatous plaque or not based on the composition ratio, the contact-monitoring using the autofluorescence spectrum difference can perform diagnosis more precisely than IVUS (intravascular ultrasound), with which it is determined whether there is an atheromatous plaque or not based on the size of the blood vessel diameter.

Fifth Embodiment

According to the (5) cytocidal-effect-determining operation of the first embodiment, during photodynamic therapy, it is determined whether there is a cytocidal effect or not (FIG. 5, Step S113). Meanwhile, according to a fifth embodiment, during photodynamic therapy, the contact state of the tip portion of the laser catheter with respect to an inner wall of a tissue is determined in addition to determining whether there is a cytocidal-effect.

Specifically during intracardiac therapy using a laser catheter, the laser catheter moves affected by breathing and heartbeat, and the contact state with respect to a therapy-target tissue may change. Because of this, even if the contact state of the tip portion of the laser catheter is confirmed before emitting an excitation light (FIG. 5, Step S106), it is preferable to monitor how the contact state of the tip portion of the laser catheter changes during photodynamic therapy also. Further, in PDT, even if therapy is performed under the same irradiation conditions (irradiation time, irradiation power), the amount of generated singlet oxygen in a therapy-target site varies. Because of this, in order to reliably perform therapy, it is preferable to also monitor the PDT process status (cytocidal effect) in real time. One reason of the variable amount of generated singlet oxygen is the individual variability of pharmaceutical concentration (in case of pharmaceutical concentration of Laserphyrin in blood plasma, plus or minus 10 to 20%). Because amounts of light, pharmaceutical, and oxygen greatly contribute to PDT therapeutic effects, in the case where the pharmaceutical concentration is low, the enough therapeutic effect may not be obtained. Another reason is that, in some therapy-target sites, it is difficult to control the intracardiac posture of the tip portion of the laser catheter such that the posture is the identical contact state (upright-contact state). In the case of the slanting-contact state or the non-contact state of the tip portion of the laser catheter, the effective optical-energy input amount in a tissue is decreased. As a result, if the irradiation time is not made longer or the set irradiation power is not increased, the therapeutic effect may not be enough. In order to solve such problems, the PDT process level (cytocidal effect) and the contact state of the tip portion of the laser catheter in a therapy-target tissue are monitored in real time, and the irradiation conditions may be set/changed according to the status.

As methods of monitoring the contact state of the tip portion of the laser catheter during therapeutic-light irradiation, for example, a radioscopic image and potential measurement (impedance measurement) are known. However, in the case of using a radioscopic image, because it is necessary to keep on fluoroscoping during an operation, there is a problem in that the radiation-exposure amount of a patient and a practitioner is extremely large. Meanwhile, in the case of using potential measurement (impedance measurement), because a catheter having an electrode at the tip portion is used in the case of cardiac-disease therapy using a catheter, the contact state may be grasped roughly before the therapy based on its potential. However, because a cardiomyocyte loses its electric conductivity and the potential is decreased after starting therapy, the potential may not be observed even if the contact state is maintained. In other words, there is a problem in that it is not possible to detect how the contact state of the tip portion of the catheter changes during therapy.

In view of the above-mentioned circumstances, according to this embodiment, a cytocidal effect is estimated and the contact state of the tip portion of a laser catheter with respect to an inner wall of a tissue is determined during photodynamic therapy, based on intensity of detected fluorescence.

Figure 20:
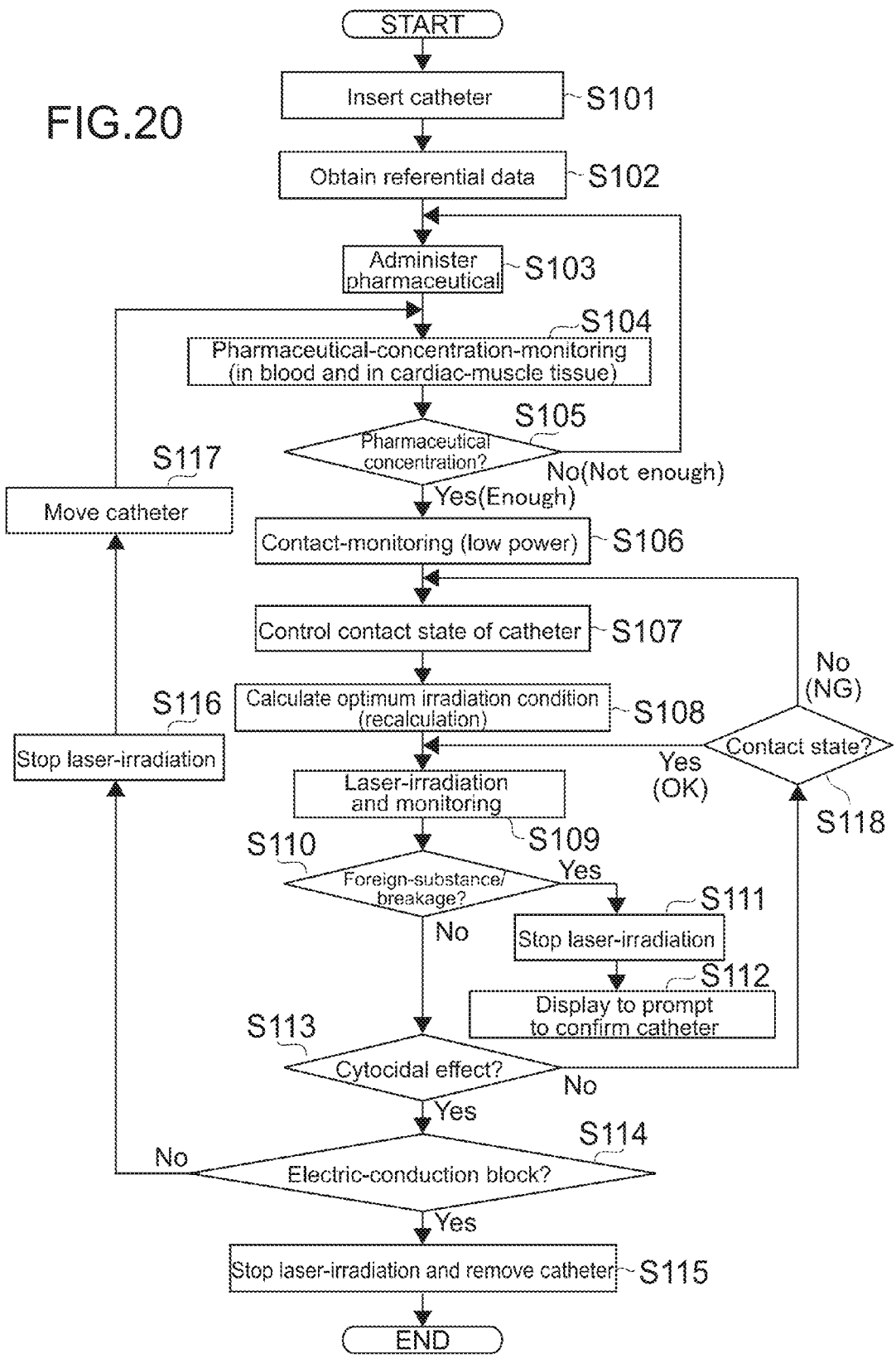
FIG. 20 A flowchart showing operations of the PDT apparatus.

FIG. 20 is a flowchart showing operations of the PDT apparatus.

The operations of the PDT apparatus shown in FIG. 20 are different from the operations of the PDT apparatus shown in FIG. 5 in that, after it is not determined that there is a cytocidal effect (Step S113, No), the contact state of the tip portion of the laser catheter is determined (Step S118).

After it is not determined that there is a cytocidal effect (Step S113, No), continuously, the light source 110 outputs the excitation light with the second intensity to the optical system 120, which is started in Step S109, the controller 150 calculates fluorescence intensity, and the display unit 170 displays the temporal change of fluorescence intensity on the display screen. For example, the display unit 170 displays the temporal change of fluorescence intensity on the display screen as a graph.

Here, an example of a graph showing the temporal change of fluorescence intensity will be described.

Figure 21:
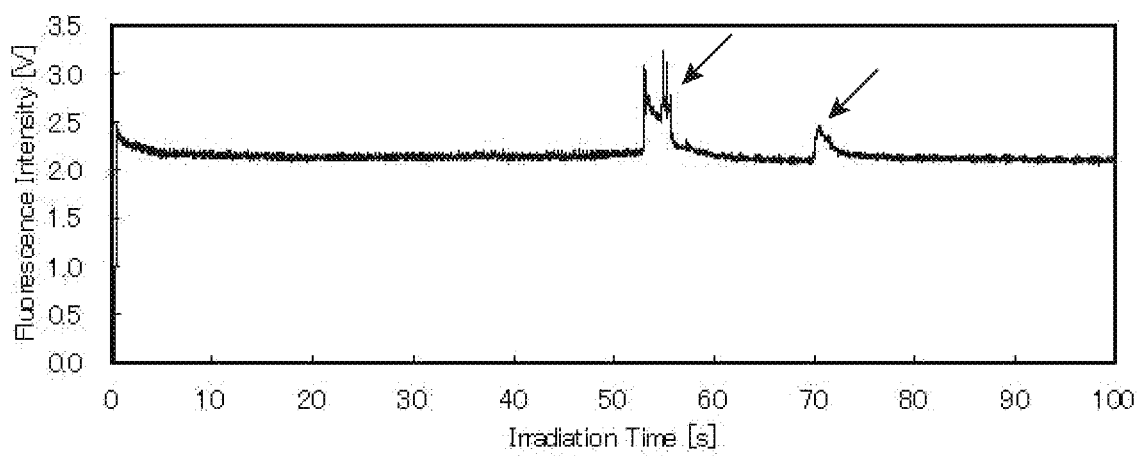
FIG. 21 A graph showing a temporal change of fluorescence intensity.

FIG. 21 is a graph showing the temporal change of fluorescence intensity.

FIG. 21 shows an example in which irradiation is started under the identical contact state (upright-contact state). At the two time points with arrows, the fluorescence intensity has large values. As described above, the pharmaceutical concentration in blood is higher than the pharmaceutical concentration in a cardiac-muscle tissue. In view of this, a practitioner understands that the tip portion of the laser catheter is removed from a cardiac-muscle tissue and contacts blood at the two time points at which the fluorescence intensity has large values. When a practitioner detects the change, the practitioner operates a handpiece or the like (not shown.), to thereby return the posture of the tip portion of the laser catheter to the identical contact state (upright-contact state) (Step S118, No). Note that, in the state where the contact state of the tip portion of the laser catheter is preferable, the posture of the tip portion of the laser catheter is not controlled, and the controller 150 controls to continuously output the excitation light with the second intensity to the optical system 120 (Step S118, Yes). Further, a pharmaceutical bleaching (attenuation of fluorescence amount) status, which relates to the PDT process level, is reflected in the graph shown in FIG. 21.

As described above, according to this embodiment, a practitioner simultaneously monitors the PDT process level (cytocidal effect) and the contact monitoring in real time during therapeutic-light irradiation, and, in the case where the posture of the laser catheter is not the upright-contact state, may control the posture again. Then, in the case where the PDT process level (cytocidal effect) reaches the appropriate range, the practitioner may stop irradiation.

Sixth Embodiment

In the fifth embodiment, the contact state of the tip portion of the laser catheter is estimated based on the increased amount of fluorescence as an index, and the PDT process level (cytocidal effect) is estimated based on the attenuation amount of fluorescence as an index. However, in the case where the PDT process level (cytocidal effect) is estimated based on the attenuation amount of fluorescence as an index, a practitioner may feel unconformity when the index is decreased as therapy progresses, sensuously. Further, there is not established a method of determining the PDT process level (cytocidal effect) in view of variations and differences of irradiation conditions and pharmaceutical-administration conditions.

To the contrary, according to a sixth embodiment, the PDT process level (cytocidal effect) is estimated in view of variations and differences of irradiation conditions and pharmaceutical-administration conditions, and, simultaneously, the contact state of the tip portion of a laser catheter with respect to an inner wall of a tissue is determined.

Figure 22:
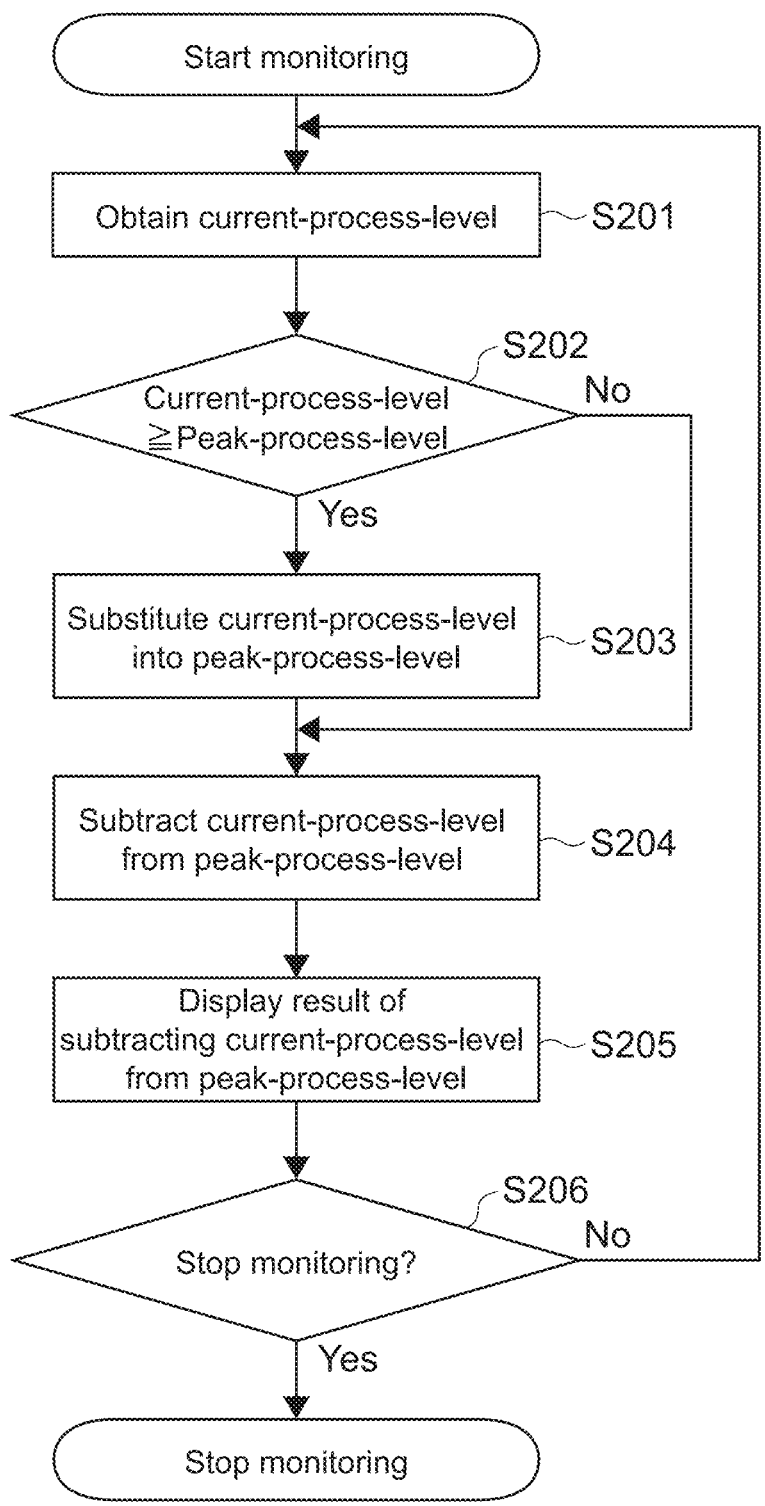
FIG. 22 A flowchart showing a monitoring operation of PDT process level and a contact state.

FIG. 22 is a flowchart showing a monitoring operation of PDT process level and a contact state.

The monitoring operation of PDT process level and a contact state is performed in, for example, Step S113 (cytocidal-effect-determining operation) of the flowchart of FIG. 5 or FIG. 20.

First, the controller 150 calculates the present value of the PDT process level (hereinafter, referred to as "current-process-level") based on fluorescence intensity (Step S201).

Here, a method of calculating PDT process level will be described.

Figure 23:
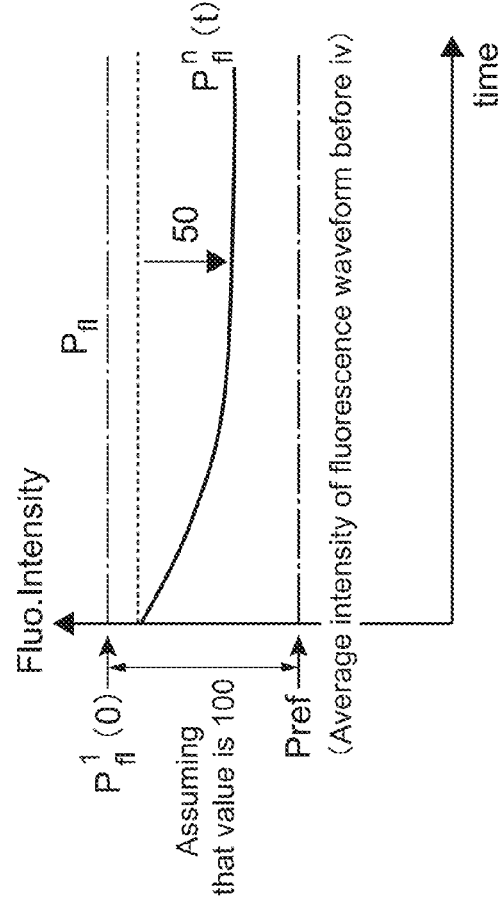
FIG. 23 A diagram for explaining formulae for calculating PDT process level.

FIG. 23 is a diagram for explaining formulae for calculating PDT process level.

In the formulae, $P_{fl}$ is fluorescence intensity, n is a variable indicative of the number of excitation-light-irradiation times (for example, n=1 is indicative of irradiation after 15 minutes after pharmaceutical administration, n=2 is indicative of the same after 16 minutes, and n=3 is indicative of the same after 16 minutes 30 seconds . . . ), and t is a variable indicative of an irradiation time period. For example, $P_{fl}^1(0)$ is indicative of the state where the first (i.e., n=1) excitation-light irradiation is started (i.e., t=0), that is, of an initial value of fluorescence intensity ($P_{fl}$) before excitation-light irradiation. Pref is indicative of an average intensity (background) of a fluorescence waveform in the case where the excitation light is emitted before pharmaceutical administration. That is, $P_{fl}^1(0)$-Pref is indicative of fluorescence intensity at a predetermined time after pharmaceutical administration and before excitation-light irradiation, which is an initial value (in this example, 100). Further, X (mg/kg) is a variable indicative of a pharmaceutical-administration amount, and P (W/cm2) is a variable indicative of an excitation-light-irradiation power.

This estimating method continuously calculates the amount of attenuation of fluorescence intensity every irradiation immediately after starting irradiation, in the case where the fluorescence intensity difference before and after pharmaceutical administration is 100 under certain referential conditions (for example, the pharmaceutical-administration amount is 10 mg/kg, and the irradiation power is 40 W/cm2). Here, 10 mg/kg is an arbitrarily-selected value as a peak value in a range, in which there is no toxicity to a living body, and 40 W/cm2 is an arbitrarily-selected value as a peak value of an irradiation power in a range, in which extremely small or no burning occurs. As such a correlation between concentration and irradiation power during pharmaceutical administration, a standard condition, which is determined by experimentally searching for a condition, may be used. Further, also in the case of a condition other than a referential condition, in order to relatively compare the amount of generated singlet oxygen, which affects therapeutic effects, it is possible to perform calculation in view of factors of a pharmaceutical-administration amount and an irradiation power.

Alternatively, the correlation between concentration and irradiation power during pharmaceutical administration may be set as follows, instead of using a standard condition, which is determined by experimentally searching for a condition.

Figure 24:
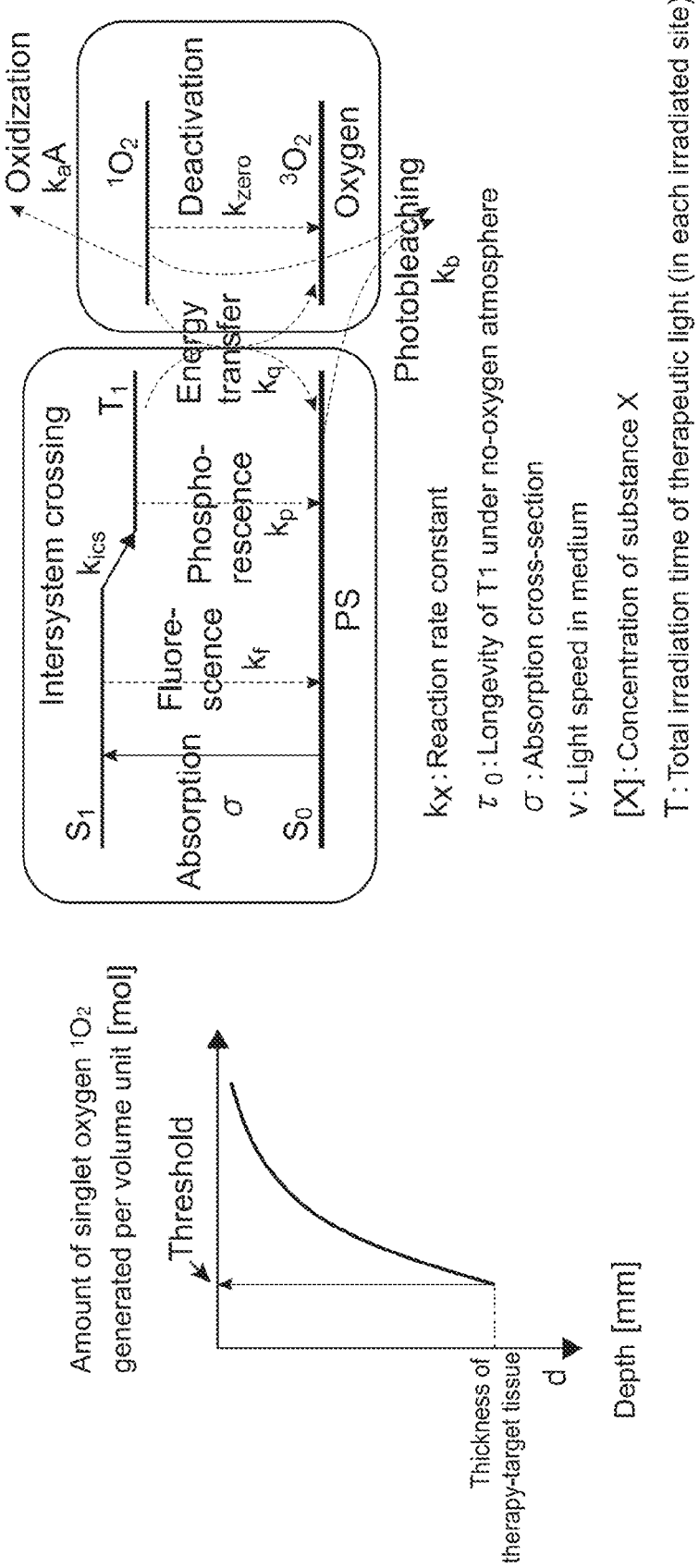
FIG. 24 A diagram for explaining a method of calculating PDT process level.

FIG. 24 is a diagram for explaining a method of calculating PDT process level.

It is necessary to set the concentration (PS dose) and the irradiation power I during pharmaceutical administration such that the amount of singlet oxygen generated in the lowermost layer of a therapy-target tissue (in ellipse of FIG. 25) per volume unit exceeds a threshold of the amount of generated singlet oxygen, which induces cell-death. In the formulae of FIG. 24 and FIG. 25, $k_x$ is indicative of reaction rate constant, $\tau_0$ is indicative of longevity of $T_1$ under a no-oxygen atmosphere, σ is indicative of absorption cross-section, v is indicative of light speed in a medium, [X] is indicative of concentration of a substance X, and T is indicative of the total irradiation time of a therapeutic light in each irradiated site.

FIG. 25 shows formulae for setting concentration and an irradiation power during pharmaceutical administration.

In the formulae, t is indicative of an irradiation time period in each site, t' is indicative of an elapsed time after pharmaceutical administration, and ρ is indicative of a light density at depth d. Pharmaceutical concentration in a tissue $[S_0]_t(t)$ is a function of PS dose, time t, and time t', in which PS dose is concentration during pharmaceutical administration (pharmaceutical amount with respect to body weight). However, in general, pharmaceutical concentration is unknown without actual measurement, most of the time. However, at present, there is no useful method of actually measuring a temporal change of pharmaceutical concentration in a tissue of the same individual. According to this embodiment, it is possible to actually measure a temporal change of pharmaceutical concentration in a tissue of the same individual.

Figure 26:
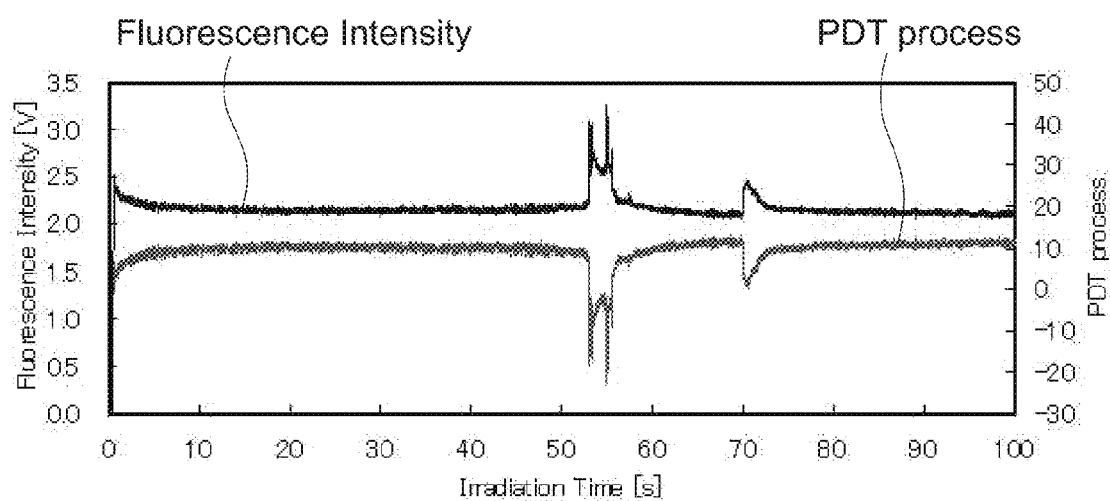
FIG. 26 A graph showing a PDT process level calculated based on the formulae of FIG. 23.

FIG. 26 is a graph showing a PDT process level calculated based on the formulae of FIG. 23.

By using the formulae of FIG. 23, it is possible to transform fluorescence intensity (see FIG. 21) into PDT process level (PDT progress). The controller 150 starts to record, in the storage 160, the temporal change of the PDT process level as a log in which the calculated PDT process level is in relation with time information obtained from a timing measurement unit (not shown.). Further, the controller 150 records the peak value out of the recorded PDT process level in the storage 160 as the peak-process-level. Further, the controller 150 may create display information of the temporal change of the PDT process level based on the calculated PDT process level and the elapsed time after the criterion time, which is the irradiation-start time in each irradiated-site, and may output display instruction including the created display information to the display unit 170. The display unit 170 obtains the display instruction from the controller 150, and then displays the temporal change of the PDT process level on the display screen based on the display information included in the display instruction. For example, the display unit 170 displays the temporal change of the PDT process level on the display screen in a graph form shown in FIG. 26 or FIG. 27.

Figure 27:
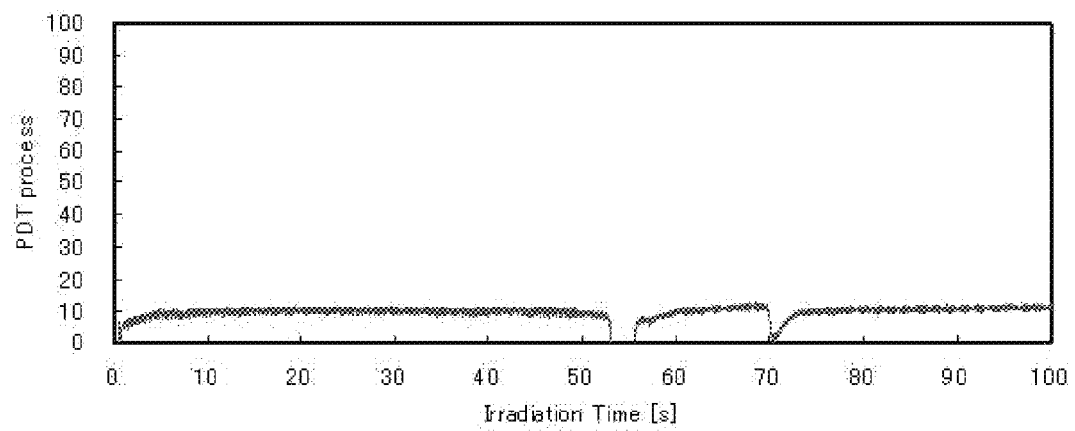
FIG. 27 A graph showing a modified example of the graph of FIG. 26.

FIG. 27 is a graph showing a modified example of the graph of FIG. 26.

As shown in FIG. 27, the scale of the temporal change of PDT process level may be fixed to 0 to 100. Here, 0 is indicative of the background before pharmaceutical administration, and 100 is indicative of the maximum fluorescence intensity immediately after irradiation is started at the time of high-power irradiation at a certain criterion time.

With reference to FIG. 22 again, the controller 150 calculates the current-process-level (Step S201), and then starts an estimating operation of the contact state of the tip portion of the laser catheter (Step S202 to Step S205).

The contact state is estimated based on the difference between the peak-process-level and the current-processlevel. Here, the principle will be described. In the case of pinpoint-irradiating a cardiac-muscle tissue by using a laser catheter, pharmaceutical is consumed in the site (cardiac-muscle tissue), and, as a result, fluorescence intensity is decreased. Because PDT process level is increased temporally as fluorescence intensity is decreased, the current-process-level may be continuously updated with the peak value (peak-process-level). However, if the laser catheter is removed from a cardiac-muscle tissue and drifts in blood, a fluorescence signal in blood, whose pharmaceutical concentration is higher than the pharmaceutical concentration in a cardiac-muscle tissue, is added, and the fluorescence intensity is increased. As the fluorescence intensity is increased, the PDT process level is decreased. As a result, in the case where the laser catheter drifts in blood, a difference between the current-process-level and the peak-process-level, which should not be generated essentially, may be generated. In this embodiment, the difference is used to estimate a contact state.

First, the controller 150 compares the current-process-level, which is calculated based on the formulae of FIG. 23 in Step S201, with the peak-process-level recorded in the storage 160 (Step S202). If the controller 150 determines that the current-process-level is equal to or larger than the peak-process-level (Step S202, Yes), the controller 150 updates the peak-process-level recorded in the storage 160 with the current-process-level (Step S203).

Meanwhile, if the controller 150 determines that the current-process-level is less than the peak-process-level (Step S202, No), the value of the current-process-level, which should be the peak-process-level essentially, is decreased below the peak-process-level. Specifically, the laser catheter is removed from a cardiac-muscle tissue and drifts in blood, the fluorescence signal in blood is added, and the fluorescence intensity is increased.

Subsequently, the controller 150 subtracts the current-process-level from the peak-process-level (Step S204). In the case where the peak-process-level is updated with the current-process-level (Step S203), the subtraction result is 0, which means that the contact state, which is confirmed at the low power (first intensity) before the laser catheter starts therapeutic-light irradiation (Step S106), is maintained, or means that the contact state immediately after irradiation is started is maintained. Meanwhile, in the case where the value of the current-process-level is decreased below the peak-process-level (Step S202, No), the subtraction result is larger than 0, which means that there is a gap between the laser catheter and a cardiac-muscle tissue, that is, means the slanting-contact state or means that the laser catheter is changed to the state where it drifts in blood.

The controller 150 creates display information of the contact state of the tip portion of the laser catheter based on the subtraction result, and outputs display instruction including the created display information to the display unit 170. Specifically, the controller 150 visually reflects the peak-process-level in the current-process-level to thereby create display information for informing of the contact state of the tip portion of the laser catheter, based on the difference between the current-process-level and the peak-process-level, and outputs display instruction including the created display information to the display unit 170 (Step S205). The display unit 170 obtains the display instruction from the controller 150, and then displays information of the contact state of the tip portion of the laser catheter on the display screen, based on the display information included in the display instruction. For example, the display unit 170 displays information of the PDT process level and of the contact state of the tip portion of the laser catheter on the display screen.

Here, a display mode of information of the PDT process level and of the contact state of the tip portion of the laser catheter will be described.

Figure 28:
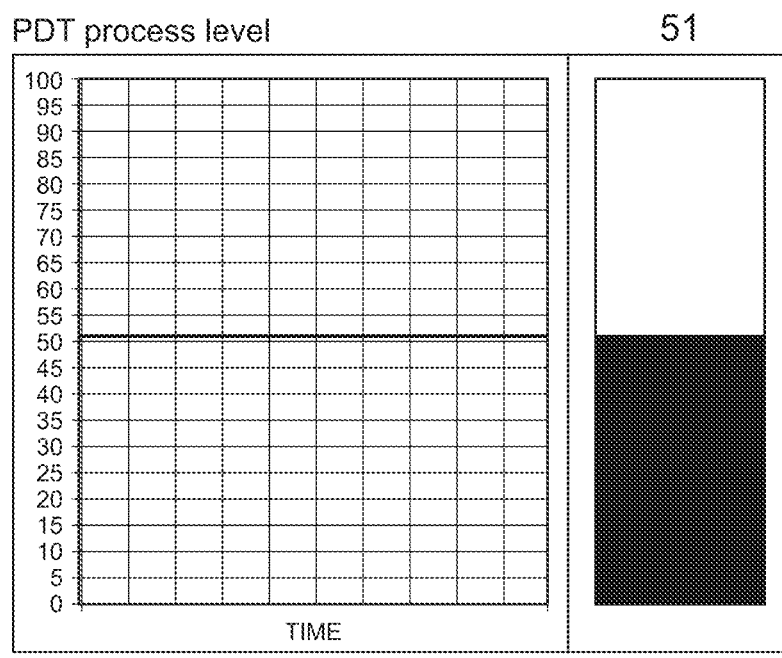
FIG. 28 A display window displaying the PDT process level and the contact state of the tip portion of the laser catheter.

FIG. 28 is a display window displaying the PDT process level and the contact state of the tip portion of the laser catheter.

The left graph in FIG. 28 (hereinafter, referred to as time-waveform display) shows the temporal change of PDT process level, and the scale is fixed to 0-100. The right index in FIG. 28 (hereinafter, referred to as level-meter display) simultaneously shows the current-process-level and the peak-process-level, and shows the difference between the current-process-level and the peak-process-level. Further, the numerical value (51 a.u.) showing the current-process-level is simultaneously displayed.

FIG. 28 shows an example in which the peak-process-level coincides with the current-process-level. In the case where the peak-process-level coincides with the current-process-level, there is no difference between the peak-process-level and the current-process-level, and difference is thus not displayed. In view of this, a practitioner may recognize that the contact state of the tip portion of the laser catheter is not changed from the contact state, which is confirmed at the low power (first intensity) before therapeutic-light irradiation is started (Step S106), or from the contact state immediately after irradiation is started.

Figure 29:
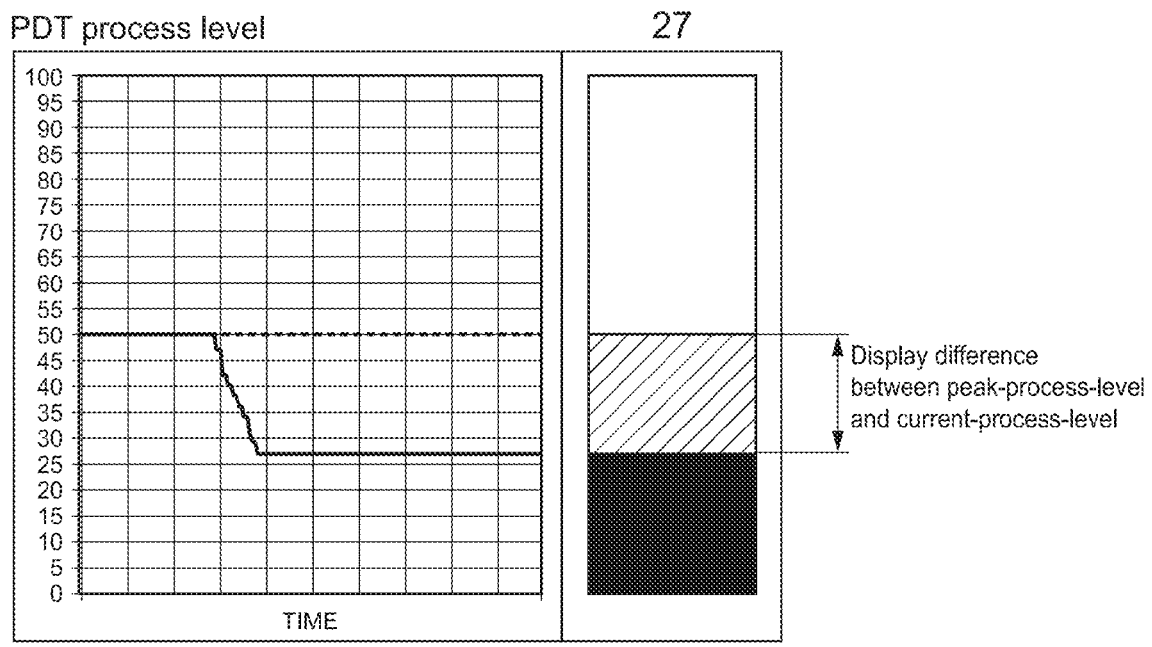
FIG. 29 Another display window displaying the PDT process level and the contact state of the tip portion of the laser catheter.

FIG. 29 is another display window displaying the PDT process level and the contact state of the tip portion of the laser catheter.

FIG. 29 is an example in which there is a difference between the peak-process-level and the current-process-level. In the time-waveform display, the solid line shows the temporal change of PDT process level, and the dashed line shows the peak-process-level. In the example shown in FIG. 29, after therapy is started, the controller 105 continuously updates the peak-process-level for about 3 seconds, the current-process-level is decreased after that, and the difference between the current-process-level and the peak-process-level is generated.

In the level-meter display, the current-process-level (27 a.u.) is displayed on the peak-process-level (about 51 a.u.) in an overlapped manner. In view of this, a practitioner may recognize the difference between the peak-process-level and the current-process-level, which is the hatched range in FIG. 29, as the change of the contact state of the tip portion of the laser catheter. Specifically, the practitioner may recognize that the contact state of the tip portion of the laser catheter has changed from the contact state, which is confirmed at the low power (first intensity) before therapeutic-light irradiation is started (Step S106), or from the contact state immediately after irradiation is started, and that the tip portion of the laser catheter is in a further-slanting-contact state or in the non-contact state.

Figure 30:
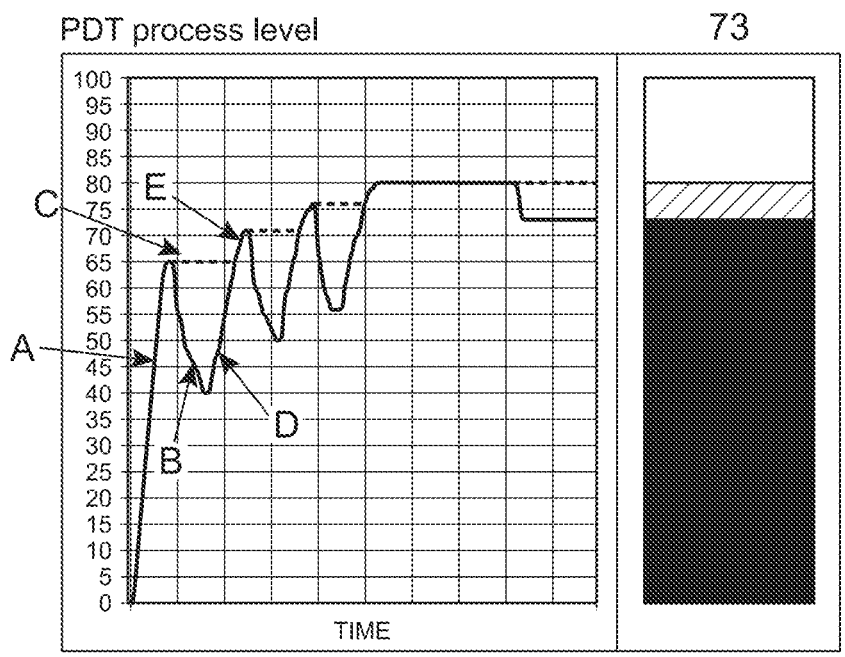
FIG. 30 Another display window displaying the PDT process level and the contact state of the tip portion of the laser catheter.

FIG. 30 is another display window displaying the PDT process level and the contact state of the tip portion of the laser catheter.

In the time-waveform display, after therapy is started, the controller 105 continuously updates the peak-process-level for about 1 second (arrow A). It means that PDT progresses while maintaining the contact state, which is confirmed at the low power (first intensity) before the laser catheter starts therapeutic-light irradiation (Step S106), or maintaining the contact state immediately after irradiation is started. After that, the current-process-level is decreased for a while (arrow B). It means that the laser catheter is removed from a cardiac-muscle tissue gradually, and the area of the tip portion of the laser catheter, which contacts blood, is increased. During this period, the controller 105 does not update the peak-process-level, and keeps on displaying, as the peak-process-level, the peak-process-level immediately before the current-process-level starts to be decreased (arrow C). A practitioner refers to the display screen, recognizes that the contact state of the tip portion of the laser catheter has changed from the contact state, which is confirmed at the low power (first intensity) before therapeutic-light irradiation is started (Step S106), or from the contact state immediately after irradiation is started, and then controls the posture of the tip portion of the laser catheter. As a result, when the laser catheter returns to the upright-contact state, the current-process-level is continuously increased for a while again (arrow D). When the current-process-level exceeds the peak-process-level, the controller 105 continuously updates the peak-process-level with the current-process-level (arrow E). FIG. 30 shows the case where the above-mentioned operations are repeated.

In the level-meter display, the current-process-level (73 a.u.) is displayed on the peak-process-level (about 80 a.u.) in an overlapped manner. As a result, a practitioner may recognize the difference between the peak-process-level and the current-process-level, which is shown as the hatched range in FIG. 30, as the change of the contact state of the tip portion of the laser catheter, intuitively. Specifically, a practitioner may recognize intuitively that the contact state of the tip portion of the laser catheter has changed from the contact state, which is confirmed at the low power (first intensity) before therapeutic-light irradiation is started (Step S106), or from the contact state immediately after irradiation is started, and that the laser catheter is removed from a cardiac-muscle tissue and drifts in blood.

With reference to FIG. 22 again, a practitioner refers to the PDT process level and the contact state of the tip portion of the laser catheter, which are displayed in Step S205, and determines whether to stop the monitoring operation of PDT process level and a contact state, or not. In the case of stopping the monitoring operation of PDT process level and a contact state, the practitioner performs a predetermined input operation in the operating unit 180 to stop the monitoring operation. The operating unit 180 receives the instruction to stop the monitoring operation, which is input through the input operation by the practitioner, and outputs the received instruction to the controller 150. Based on the instruction from the operating unit 180, the controller 150 stops the monitoring operation (Step S206, Yes). Meanwhile, if the practitioner does not perform the input operation in the operating unit 180, the controller 150 continuously performs the monitoring operation of PDT process level and a contact state (Step S206, No).

According to this embodiment, the controller 150 visually reflects a peak-estimated-result (peak-process-level) of a change of a tissue in a current-estimated-result (current-process-level) of a change of a tissue, and simultaneously informs a practitioner of the estimated result of a change of a tissue and the contact state of the tip portion of the laser catheter. As a result, a practitioner may recognize the current-estimated-result (current-process-level) of a change of a tissue and the contact state of the tip portion of the laser catheter simultaneously and intuitively. As a result, during therapeutic-light irradiation, a practitioner may recognize that the tip portion of the laser catheter has been removed affected by heartbeat or breathing in real time, and may control the posture promptly. Simultaneously, a practitioner may understand the PDT process level, which may vary according to individual variability and therapy-target sites, accurately in real time, and perform the operation. A practitioner such as a doctor needs to determine everything with reference to a plurality of screens displaying, for example, radioscopic images and the like during an operation. So it is helpful for a trouble-free operation by a practitioner to display the current-estimated-result (current-process-level) of a change of a tissue and the contact state of the tip portion of the laser catheter in an intuitively-recognizable mode.

Seventh Embodiment

The display mode of PDT process level and the contact state of the tip portion of a laser catheter may be a display mode different from the display mode shown in each of the above-mentioned FIG. 28 to FIG. 30. According to the above-mentioned sixth embodiment, the peak-process-level is visually reflected in the current-process-level, and a display window, which informs a practitioner of the contact state of the tip portion of the laser catheter, is displayed. Meanwhile, according to a seventh embodiment, a display window, which displays the current-process-level and information to inform of the contact state of the tip portion of a laser catheter separately, is displayed.

Figure 31:
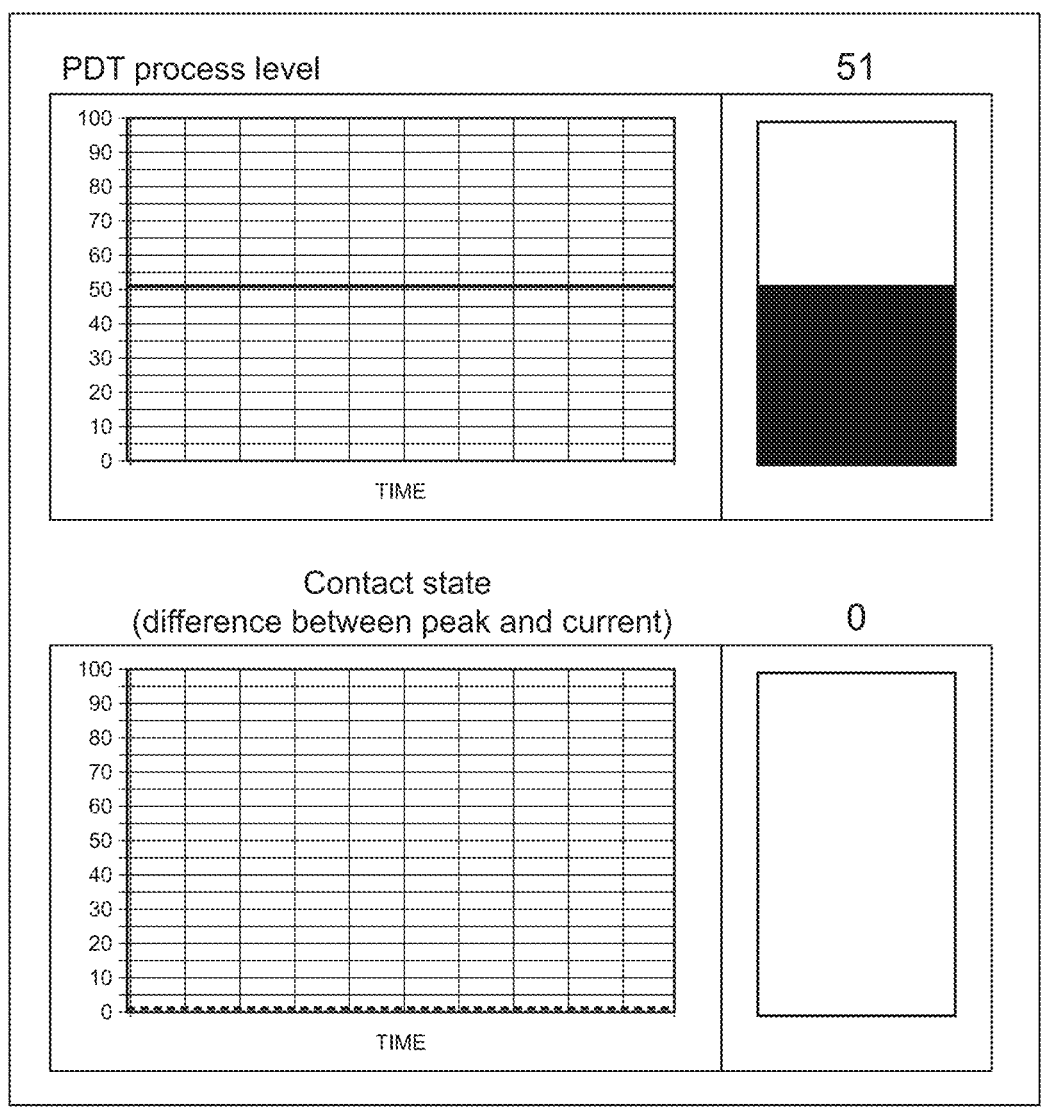
FIG. 31 Another display window displaying the PDT process level and the contact state of the tip portion of the laser catheter.

FIG. 31 is another display window displaying PDT process level and the contact state of the tip portion of a laser catheter.

In the upper area of FIG. 31, the time-waveform display showing the temporal change of PDT process level, the level-meter display showing the current-process-level, and the numerical value (51) showing the current-process-level are displayed. In the lower area of FIG. 31, the time-waveform display, which shows the temporal change of the difference between the peak-process-level and the current-process-level as the contact state of the tip portion of a laser catheter, the level-meter display, which shows the difference between the current-process-level and the peak-process-level (51) as the current contact state of the tip portion of the laser catheter, and the numerical value (0=51−51), which shows the contact state, are displayed. Here, it is understood that, as the numerical value showing the contact state is smaller, the contact state of the tip portion of the laser catheter changes less, and as the numerical value is larger, the contact state of the tip portion of the laser catheter changes more, and a gap between the laser catheter and a cardiac-muscle tissue is larger. Because the numerical value showing the contact state is 0, a practitioner may recognize that the contact state of the tip portion of the laser catheter has not changed.

Figure 32:
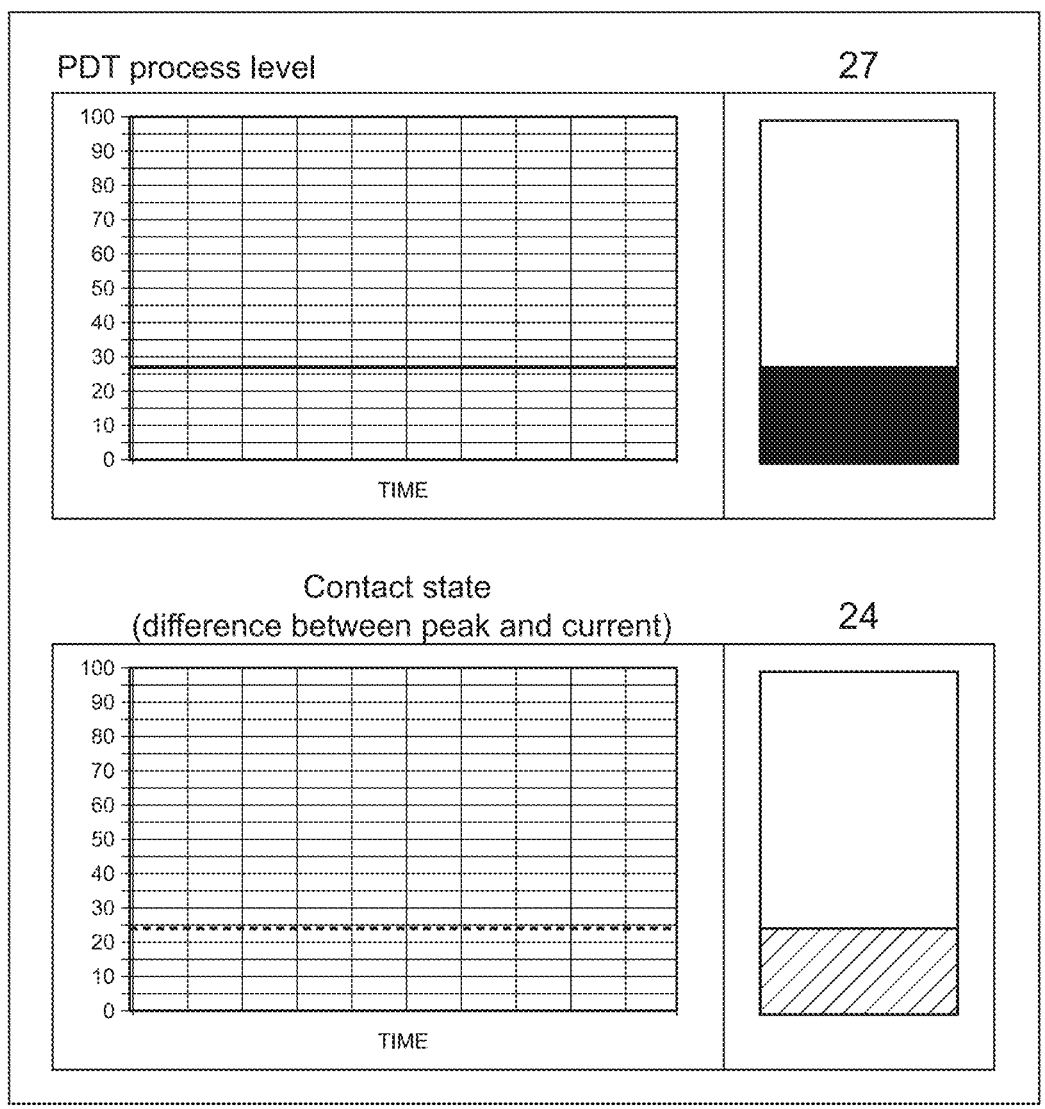
FIG. 32 Another display window displaying the PDT process level and the contact state of the tip portion of the laser catheter.

FIG. 32 is another display window displaying PDT process level and the contact state of the tip portion of a laser catheter.

In the upper area of FIG. 32, the time-waveform display showing the temporal change of PDT process level, the level-meter display showing the current-process-level, and the numerical value (27) showing the current-process-level are displayed. In the lower area of FIG. 32, the time-waveform display, which shows the temporal change of the difference between the peak-process-level (51) and the current-process-level as contact states of the tip portion of the laser catheter, the level-meter display, which shows the difference between the current-process-level and the peak-process-level as the current contact state of the tip portion of the laser catheter, and the numerical value (24=51−27), which shows the contact state, are displayed. Because the numerical value showing the contact state is 24, a practitioner may recognize that the contact state of the tip portion of the laser catheter has changed to the slanting-contact state.

Eighth Embodiment

According to the above-mentioned sixth embodiment, as an index showing the contact state of the tip portion of the catheter 300, the difference between the peak-process-level and the current-process-level of PDT is used. To the contrary, according to the eighth embodiment, as an index showing the contact state of the tip portion of the catheter 300, the difference between the minimum value and the present value of fluorescence intensity is used.

In this case, in the flowchart of FIG. 22, Step S201 is omitted, and first, the controller 150 compares the present value with the minimum value of fluorescence intensity (Step S202). The controller 150 determines that the present value of fluorescence intensity is equal to or smaller than the minimum value (Step S202, Yes), and then updates the minimum value of fluorescence intensity with the present value (Step S203).

Meanwhile, in the case where the controller 150 determines that the present value of fluorescence intensity is larger than the minimum value (Step S202, No), the present value of fluorescence intensity, which ought to be the minimum value essentially, rises above the minimum value. Specifically, the laser catheter is removed from a cardiac-muscle tissue and drifts in blood, and a fluorescence signal from blood is added to increase the fluorescence intensity.

Subsequently, the controller 150 subtracts the minimum value from the present value of fluorescence intensity (Step S204). If the subtraction result is 0, the laser catheter is in the identical contact state (upright-contact state). Meanwhile, if the subtraction result is larger than 0, the laser catheter is removed from a cardiac-muscle tissue and drifts in blood.

Subsequently, the controller 150 visually reflects the minimum value in the present value of fluorescence intensity, creates display information to inform of the contact state of the tip portion of the laser catheter, and outputs display instruction including the created display information to the display unit 170 (Step S205).

Ninth Embodiment

According to the above-mentioned sixth embodiment, during the excitation light is output with the high-power second intensity, which is used for therapy, the contact state of the tip portion of the laser catheter with respect to an inner wall of a tissue is displayed intuitively. To the contrary, according to the ninth embodiment, during the excitation light is output with the low-power first intensity, the contact state of the tip portion of the laser catheter with respect to an inner wall of a tissue is displayed intuitively.

The low-power contact-monitoring operation is performed in a waiting time (interval time) between administration of pharmaceutical by intravenous injection and the start of therapy by outputting the excitation light with the second intensity. For example, the low-power contact-monitoring operation is performed in Step S104 (pharmaceutical-concentration-monitoring operation) or in Step S106 or S107 (contact-monitoring operation) in the flowchart of FIG. 5 or FIG. 20. Further, the low-power contact-monitoring operation may be performed every time the excitation light is output with the second intensity, that is, every time before therapy is performed, or may be omitted. Further, in the case where a patient is a human, if a therapy time period is long such as 3 hours, the low-power contact-monitoring operation may be performed again as correction. However, because it is considered that the pharmaceutical concentration is approximately constant in a basically-assumed average operation time, the low-power contact-monitoring operation is performed in a waiting time (interval time) between administration of pharmaceutical by intravenous injection and the start of therapy by outputting the excitation light with the second intensity.

Figure 34:
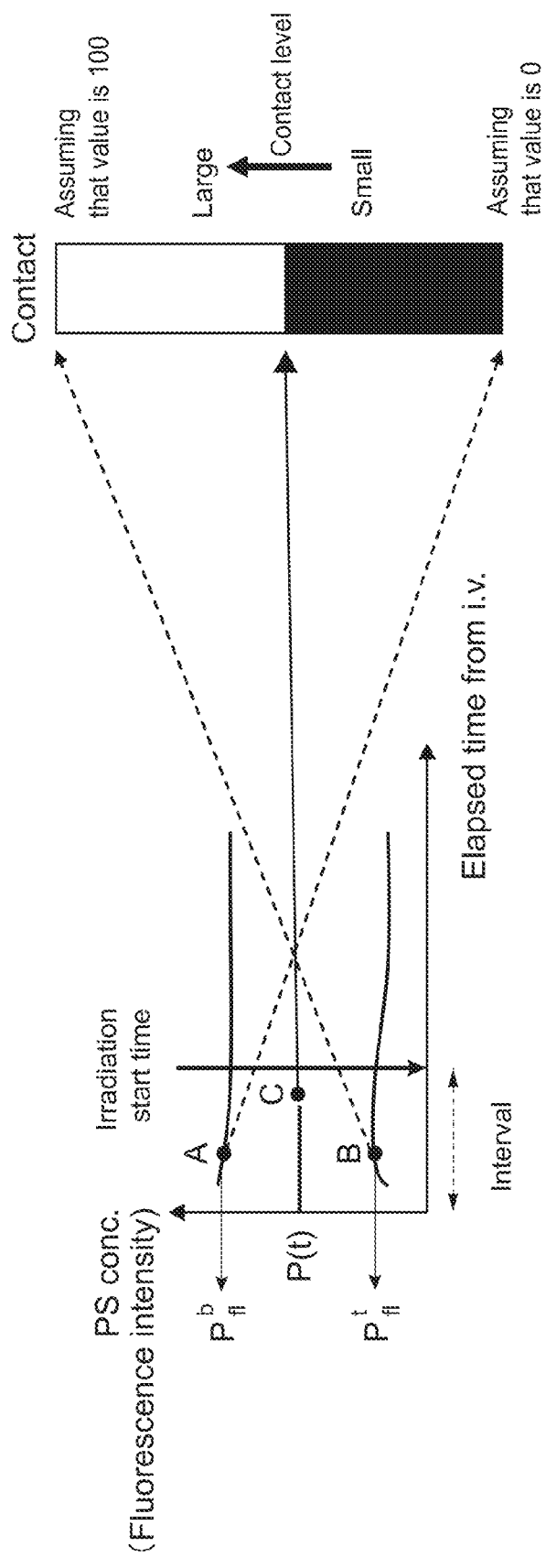
FIG. 34 A diagram for explaining method of calculating the contact level.

FIG. 33 shows a formula for calculating the contact level of the tip portion of the laser catheter with respect to an inner wall of a tissue. FIG. 34 is a diagram for explaining a method of calculating the contact level.

In FIG. 33, $P_{fl}^{b}$ is indicative of the fluorescence intensity in the non-contact state, that is, the fluorescence intensity in blood, $P_{fl}^{t}$ is indicative of the fluorescence intensity in the upright-contact state, that is, the fluorescence intensity in a tissue, and P(t) is indicative of the fluorescence intensity in an arbitrary contact state.

First, after pharmaceutical administration, a practitioner disposes the tip portion of the laser catheter in the non-contact state with respect to a tissue. When the controller 150 obtains an excitation-light-output instruction from a practitioner via the operating unit 180, the controller 150 outputs an excitation-light-output instruction with the first intensity to the light source 110, and calculates the fluorescence intensity in the non-contact state, that is, the fluorescence intensity $P_{fl}^{b}$ in blood (FIG. 34, point A), based on an electrical signal obtained from the detection unit 130. Subsequently, the practitioner disposes the tip portion of the laser catheter in the upright-contact state with respect to a tissue. Similar to the above, the controller 150 calculates the fluorescence intensity in the upright-contact state, that is, the fluorescence intensity $P_{fl}^{t}$ in a tissue (FIG. 34, point B). The controller 150 subtracts the fluorescence intensity $P_{fl}^{t}$ in a tissue from the calculated fluorescence intensity $P_{fl}^{b}$ in blood, and sets the calculated value ($P_{fl}^{b} - P_{fl}^{t}$) as the peak value of the contact level.

Subsequently, a practitioner causes the tip portion of the laser catheter to contact a tissue in an arbitrary posture for therapy. The controller 150 obtains the excitation-light-output instruction from a practitioner through the operating unit 180, then outputs an excitation-light-output instruction with the first intensity to the light source 110, and calculates the fluorescence intensity P(t) in the arbitrary-posture contact state (FIG. 34, point C), based on the electrical signal obtained from the detection unit 130. The controller 150 starts to record, in the storage 160, the temporal change of the fluorescence intensity as a log in which the calculated fluorescence intensity is in relation with time information obtained from the timing measurement unit (not shown.). The controller 150 subtracts the calculated fluorescence intensity P(t) from the above-mentioned fluorescence intensity $P_{fl}^{b}$ in blood, and sets the calculated value ($P_{fl}^{b} - P(t)$) as the current contact level, which is a contact level with respect to the peak value.

The controller 150 displays the contact level of the tip portion of the laser catheter, which is calculated based on the formula of FIG. 33, in an intuitively-recognizable mode. For example, as shown in FIG. 34, the controller 150 may cause the display unit 170 to display a display window, in which the range up to the current-contact-level value is displayed on the band showing the peak value of the contact level in an overlapped manner, in a mode with which a practitioner is capable of intuitively recognizing the contact level (level-meter display).

Alternatively, the controller 150 may cause the display unit 170 to display the time-waveform display and the level-meter display in the display window in a mode with which a practitioner is capable of intuitively recognizing the temporal change of the contact level and the current contact level. Further, the contact level calculated by using the formula of FIG. 33 may be displayed as a numerical value.

Figure 35:
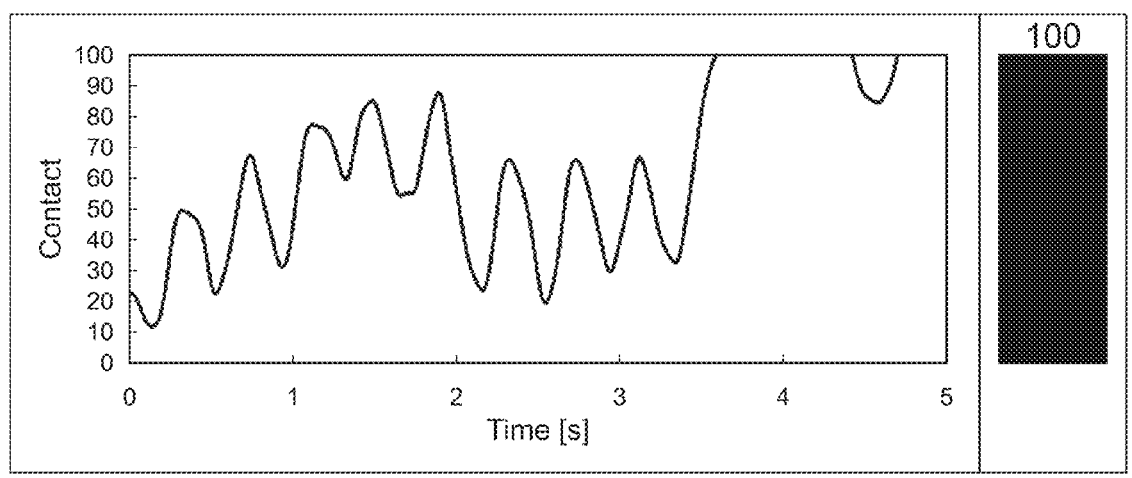
FIG. 35 A display window showing a time-waveform display and a level-meter display of a contact level.

FIG. 35 is a display window showing a time-waveform display and a level-meter display of a contact level.

In the time-waveform display, by displaying the temporal change of the contact level of the tip portion of the laser catheter with respect to a tissue with a scale of 0-100, a practitioner may recognize whether the tip portion of the laser catheter is displaced affected by heartbeat or breathing, and may control the posture promptly. Further, in the level-meter display, by displaying the current contact level of the tip portion of the laser catheter in the intuitively-recognizable mode, a practitioner may intuitively recognize the current contact state of the tip portion of the laser catheter, which the practitioner cannot see with the eyes actually. Note that, in the case where the contact level exceeds the peak value (in this example, 100), it may be displayed that the contact level equals to the peak value. Note that the current contact level may only be displayed.

Here, the relation between the contact level and the contact state of the tip portion of the laser catheter with respect to a tissue will be described.

Figure 36:
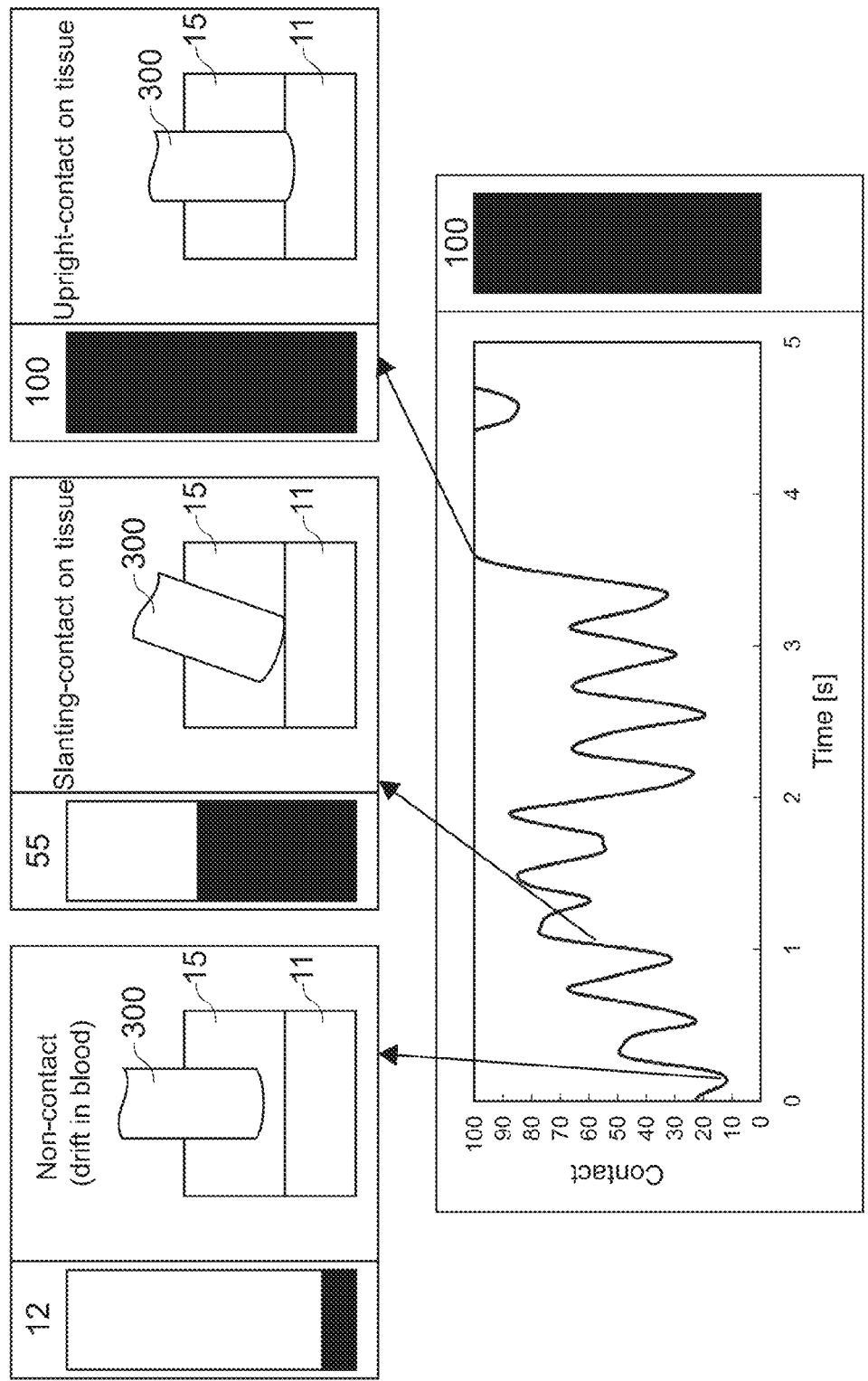
FIG. 36 A schematic diagram showing contact states of a laser catheter in a plurality of different contact levels shown in FIG. 35.

FIG. 36 is a schematic diagram showing contact states of a laser catheter in a plurality of different contact levels shown in FIG. 35.

As shown in FIG. 36, in the non-contact state, in which the blood 15 exists between the tip portion of the laser catheter and a tissue and in which the tip portion is in blood, the contact level of the tip portion of the laser catheter calculated by using the formula of FIG. 33 is, for example, 12. In the slanting-contact state, in which the tip portion of the laser catheter contacts a tissue in a slanting manner and in which the blood 15 partially exists in a gap between the tip portion and the tissue, the contact level is, for example, 55. In the upright-contact state, in which the tip portion of the laser catheter contacts the inner wall of the cardiac-muscle tissue 11 in an upright manner, the contact level is, for example, 100. A practitioner visually recognizes those contact-level values on the time-waveform display and the level-meter display, and, as a result, may intuitively recognize the current contact state of the tip portion of the laser catheter. Further, a practitioner may recognize that the tip portion of the laser catheter is displaced affected by heartbeat or breathing, and may control the posture promptly.

The embodiments of the present invention are not limited to the above-mentioned embodiments, and other various embodiments are conceivable.

Although in the above-mentioned embodiments, the laser catheter 300 is detachably connected to the connector 210 of the PDT apparatus 1, the laser catheter 300 may be provided on the PDT apparatus 1 integrally.

Although in the above-mentioned embodiments, the tube 200 is provided on the PDT apparatus main body 100 and the connector 210 is provided on the end of the tube 200, the connector 210 may be provided on the PDT apparatus main body 100.

Although in the above-mentioned embodiments, the PBS 123 is used, a DM may be used instead.

Although in the above-mentioned embodiments, the controller 150 informs a practitioner of information to prompt the predetermined controls by using the display unit 170, but is not limited to this. A speaker unit may be provided on the PDT apparatus 1, and the controller 150 may create a sound output instruction when prompting a practitioner to perform the predetermined controls, may output the created sound output instruction to the speaker unit, and may cause the speaker unit to output sounds, to thereby prompt a practitioner to perform the predetermined controls.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

DESCRIPTION OF SYMBOLS 1 photodynamic therapy (PDT) apparatus
100 PDT apparatus main body
110 light source
120, 120a optical system
121 short pass filter
122 first lens
123 polarizing beam splitter (PBS)
124 long pass filter
125 second lens
126 first dichroic mirror (DM)
127 second dichroic mirror (DM)
130, 130a detection unit
131 first photodiode (PD)
132 second photodiode (PD)
140 electrocardiograph
141 electrode pad
150 controller
160 storage
170 display unit
180 controller
200 tube
201 apparatus-attached optical fiber
210 connector
300 laser catheter
301 irradiation light
310 catheter tube
320 holder
330 optical fiber
340 optical window

The invention claimed is:

1. An estimating apparatus for therapy for atrial fibrillation, for irradiating a cardiac-muscle tissue having absorbed photo-sensitive pharmaceutical, the photo-sensitive pharmaceutical absorbing an excitation light and emitting fluorescence, with the excitation light emitted from a tip portion of a laser catheter, comprising:

a connector which the laser catheter is capable of being attached to and detached from;

a light source for outputting the excitation light to the laser catheter via the connector;

a detection unit for detecting fluorescence, the fluorescence entering the detection unit from the laser catheter via the connector, to estimate whether the cardiac-muscle tissue is changed because of reaction between the excitation light emitted from the tip portion of the laser catheter and the photo-sensitive pharmaceutical absorbed in the cardiac-muscle tissue, and whether a contact state of the tip portion of the laser catheter with respect to the cardiac-muscle tissue has changed; and a controller for simultaneously estimating whether the cardiac-muscle tissue has changed because of the reaction between the excitation light emitted from the tip portion of the laser catheter and the photosensitive pharmaceutical absorbed in the cardiac-muscle tissue, and the contact state of the tip portion of the laser catheter with respect to the cardiac-muscle tissue, the controller calculating fluorescence intensity and determining the non-contact state if the controller determines that the fluorescence intensity is equal to or larger than a first threshold; determining the upright-contact state if the controller determines that the minimum value of the fluorescence intensity is equal to or smaller than a second threshold, which is smaller than the first threshold; determining the slanting-contact state if the controller determines that the fluorescence intensity periodically fluctuates between the first threshold and the second threshold; determining whether the fluorescence intensity is attenuated below a threshold; and estimating that there is a cytocidal effect on a tissue irradiated with the excitation light if the controller determines that the fluorescence intensity is attenuated below the threshold.

2. The estimating apparatus according to claim 1, wherein the controller visually reflects a current-estimated-result of the change of the tissue in a peak-estimated-result of the change of the tissue, and outputs a signal for simultaneously informing of the estimated result of the change of the tissue and the estimated result of the contact state.

3. The estimating apparatus according to claim 2, further comprising storage for storing the peak-estimated-result of the change of the tissue, wherein the controller records the current-estimated-result of the change of the tissue in the storage, updates, in a case where the current-estimated-result of the change of the tissue is equal to or larger than the peak-estimated-result of the change of the tissue recorded in the storage, the peak-estimated-result of the change of the tissue recorded in the storage with the current-estimated-result of the change of the tissue, and outputs a signal for simultaneously informing of the estimated result of the change of the tissue and the estimated result of the contact state, by displaying the current-estimated-result of the change of the tissue on the updated peak-estimated-result of the change of the tissue in an overlapped manner.

4. The estimating apparatus according to claim 1, wherein the controller outputs a signal for informing whether the tissue has changed, based on the estimated result.

5. The estimating apparatus according to claim 1, wherein the controller outputs a signal to prompt to change an irradiation condition of the excitation light, based on the estimated result.

6. The estimating apparatus according to claim 1, wherein the controller obtains an electrocardiographic signal, and estimates whether the tissue has changed, based on a correlation between the electrocardiographic signal and the intensity of the fluorescence.

7. The estimating apparatus according to claim 1, wherein the controller visually represents a peak-estimated-result of the change of the cardiac-muscle tissue in a current-estimated-result of the change of the cardiac-muscle tissue, and outputs a signal for simultaneously informing of the estimated result of the change of the cardiac-muscle tissue and the estimated result of the contact state.

8. The estimating apparatus according to claim 7, further comprising storage for storing the peak-estimated-result of the change of the cardiac-muscle tissue, wherein the controller records the current-estimated-result of the change of the cardiac-muscle tissue in the storage, updates, in a case where the current-estimated-result of the change of the cardiac-muscle tissue is equal to or larger than the peak-estimated-result of the change of the cardiac-muscle tissue recorded in the storage, the peak-estimated-result of the change of the cardiac-muscle tissue recorded in the storage with the current-estimated-result of the change of the cardiac-muscle tissue, and outputs a signal for simultaneously informing of the estimated result of the change of the cardiac-muscle tissue and the estimated result of the contact state, by displaying the current-estimated-result of the change of the cardiac-muscle tissue on the updated peak-estimated-result of the change of the cardiac-muscle tissue in an overlapped manner.

9. An estimating method, comprising:
  irradiating a tissue having absorbed photosensitive pharmaceutical, the photo-sensitive pharmaceutical absorbing an excitation light and emitting fluorescence, with the excitation light emitted from a tip portion of a laser catheter;
  extracting the fluorescence corresponding to the irradiated excitation light via the laser catheter; and
  simultaneously estimating whether the tissue has changed because of reaction between the excitation light emitted from the tip portion of the laser catheter and the photo-sensitive pharmaceutical absorbed in the tissue, and the contact state of the tip portion of the laser catheter with respect to the tissue, based on intensity of the extracted fluorescence,
  calculating fluorescence intensity and determining the non-contact state if a controller determines that the fluorescence intensity is equal to or larner than a first threshold; determining the upright-contact state if the controller determines that the minimum value of the fluorescence intensity is equal to or smaller than a second threshold, which is smaller than the first threshold; the controller determines the slanting-contact state if the controller determines that the fluorescence intensity periodically fluctuates between the first threshold and the second threshold; determining whether the fluorescence intensity is attenuated below a threshold; and estimating that there is a cytocidal effect on a tissue irradiated with the excitation light if the controller determines that the fluorescence intensity is attenuated below the threshold.

10. The estimating method according to claim 9, further comprising: visually reflecting a current-estimated-result of the change of the tissue in a peak-estimated-result of the change of the tissue, and outputting a signal for simultaneously informing of the estimated result of the change of the tissue and the estimated result of the contact state.

11. The estimating method according to claim 10, further comprising: recording the current-estimated-result of the change of the tissue in storage, updating, in a case where the current-estimated-result of the change of the tissue is equal to or larger than the peak-estimated-result of the change of the tissue recorded in the storage, the peak-estimated-result of the change of the tissue recorded in the storage with the current-estimated-result of the change of the tissue, and outputting a signal for simultaneously informing of the estimated result of the change of the tissue and the estimated result of the contact state, by displaying the current-estimated-result of the change of the tissue on the updated peak-estimated-result of the change of the tissue in an overlapped manner.

12. The estimating method according to claim 9, further comprising:
  obtaining an electrocardiographic signal, and estimating whether the tissue has changed, based on a correlation between the electrocardiographic signal and the intensity of the fluorescence.

13. An estimating method using photo-sensitive pharmaceutical absorbing an excitation light and emitting a fluorescence, a laser catheter capable of emitting the excitation light from a tip portion, and an estimating apparatus including a connector to/from which the laser catheter is capable of being attached/detached and a light source for outputting the excitation light to the laser catheter via the connector, comprising:
- absorbing, in a tissue, the photo-sensitive pharmaceutical;
- leading the tip portion of the laser catheter to the tissue having absorbed the photo-sensitive pharmaceutical, the laser catheter being attached to the connector;
- irradiating the tissue having absorbed the photosensitive pharmaceutical with the excitation light emitted from the tip portion of the laser catheter, the excitation light being output from the light source;
- extracting the fluorescence corresponding to the irradiated excitation light via the laser catheter; and
- simultaneously estimating whether the tissue has changed because of reaction between the excitation light emitted from the tip portion of the laser catheter and the photo-sensitive pharmaceutical absorbed in the tissue, and the contact state of the tip portion of the laser catheter with respect to the tissue, based on intensity of the extracted fluorescence,
- calculating fluorescence intensity and determining the non-contact state if a controller determines that the fluorescence intensity is equal to or lamer than a first threshold; determining the upright-contact state if the controller determines that the minimum value of the fluorescence intensity is equal to or smaller than a second threshold, which is smaller than the first threshold; the controller determines the slanting-contact state if the controller determines that the fluorescence intensity periodically fluctuates between the first threshold and the second threshold; determining whether the fluorescence intensity is attenuated below a threshold; and estimating that there is a cytocidal effect on a tissue irradiated with the excitation light if the controller determines that the fluorescence intensity is attenuated below the threshold.

14. The estimating method according to claim 13, further comprising:
- visually reflecting a current-estimated-result of the change of the tissue in a peak-estimated-result of the change of the tissue, and outputting a signal for simultaneously informing of the estimated result of the change of the tissue and the estimated result of the contact state.

15. The estimating method according to claim 14, further comprising:
- recording the current-estimated-result of the change of the tissue in storage, updating, in a case where the current-estimated-result of the change of the tissue is equal to or larger than the peak-estimated-result of the change of the tissue recorded in the storage, the peak-estimated-result of the change of the tissue recorded in the storage with the current-estimated-result of the change of the tissue, and outputting a signal for simultaneously informing of the estimated result of the change of the tissue and the estimated result of the contact state, by displaying the current-estimated-result of the change of the tissue on the updated peak-estimated-result of the change of the tissue in an overlapped manner.

16. The estimating method according to claim 13, further comprising:
- obtaining an electrocardiographic signal, and estimating whether the tissue has changed, based on a correlation between the electrocardiographic signal and the intensity of the fluorescence.

* * * * *